US009759600B2

(12) United States Patent
Ichihashi

(10) Patent No.: US 9,759,600 B2
(45) Date of Patent: Sep. 12, 2017

(54) CIRCULAR POLARIZATION FILTER AND APPLICATION THEREFOR

(71) Applicant: FUJIFILM Corporation, Tokyo (JP)

(72) Inventor: Mitsuyoshi Ichihashi, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

(21) Appl. No.: 14/974,969

(22) Filed: Dec. 18, 2015

(65) Prior Publication Data
US 2016/0103015 A1 Apr. 14, 2016

Related U.S. Application Data

(63) Continuation of application No. PCT/JP2014/066371, filed on Jun. 20, 2014.

(30) Foreign Application Priority Data

Jun. 21, 2013 (JP) .................................. 2013-130633
Jul. 26, 2013 (JP) .................................. 2013-155587

(51) Int. Cl.
*G01J 1/42* (2006.01)
*G01J 1/04* (2006.01)
(Continued)

(52) U.S. Cl.
CPC ............ *G01J 1/0429* (2013.01); *G01J 1/0488* (2013.01); *G01J 1/08* (2013.01); *G02B 5/3016* (2013.01);
(Continued)

(58) Field of Classification Search
None
See application file for complete search history.

(56) References Cited

U.S. PATENT DOCUMENTS

| 6,433,853 B1 | 8/2002 | Kameyama et al. |
| 2003/0151704 A1 * | 8/2003 | Kawamoto ......... G02F 1/13362 349/96 |

(Continued)

FOREIGN PATENT DOCUMENTS

| JP | 2003-202558 A | 7/2003 |
| JP | 2003-279745 A | 10/2003 |

(Continued)

OTHER PUBLICATIONS

English translation of the International Preliminary Report on Patentability (Forms PCT/IB/338 and PCT/IB409), dated Dec. 23, 2015, for International Application No. PCT/JP2014/066371.

(Continued)

*Primary Examiner* — Yara B Green
(74) *Attorney, Agent, or Firm* — Birch, Stewart, Kolasch & Birch, LLP

(57) ABSTRACT

Provided are a circular polarization filter including a circularly-polarized light separating layer (preferably, a layer having a cholesteric liquid crystalline phase fixed therein or a laminate including a reflective linear polarizer and a λ/4 phase difference layer), in which the circularly-polarized light separating layer selectively transmits either right-handed circularly polarized light or left-handed circularly polarized light in a specific wavelength region, a transparent medium which is transparent with respect to light in the specific wavelength region is provided at least on one surface side of the circularly-polarized light separating layer, and the transparent medium has an inclined surface which forms an angle of 1° to 30° relative to the surface on the transparent medium side of the circularly-polarized light separating layer, and sensor system using the circular polarization filter. The circular polarization filter of the invention is capable of providing circularly polarized light with a high (Continued)

circular polarizance, or improving sensitivity in the sensor system using circularly polarized light.

15 Claims, 3 Drawing Sheets

(51) Int. Cl.
  *G02B 5/30* (2006.01)
  *G01J 1/08* (2006.01)
  *G01N 21/88* (2006.01)
  *G01N 21/958* (2006.01)
  *G01N 21/23* (2006.01)
  *G01N 21/84* (2006.01)
  *G01N 21/21* (2006.01)

(52) U.S. Cl.
  CPC ............ *G02B 5/3083* (2013.01); *G01N 21/23* (2013.01); *G01N 21/8422* (2013.01); *G01N 21/8806* (2013.01); *G01N 21/958* (2013.01); *G01N 2021/216* (2013.01); *G01N 2021/8848* (2013.01)

(56) References Cited

U.S. PATENT DOCUMENTS

| | | | | |
|---|---|---|---|---|
| 2007/0077404 A1* | 4/2007 | Hoshino | ............... | B32B 27/36 428/212 |
| 2007/0081144 A1* | 4/2007 | Hoshino | ................... | G09F 3/02 356/71 |
| 2009/0162625 A1* | 6/2009 | Takeuchi | ................ | G02F 1/167 428/212 |
| 2010/0086506 A1* | 4/2010 | Tanabe | ................. | A61K 8/0295 424/63 |
| 2010/0302486 A1* | 12/2010 | Hoshino | .............. | G03H 1/0011 349/115 |
| 2014/0041296 A1 | 2/2014 | Ichihashi et al. | | |

FOREIGN PATENT DOCUMENTS

| | | |
|---|---|---|
| JP | 2004-326128 A | 11/2004 |
| JP | 2013-036888 A | 2/2013 |
| WO | WO 2012/144422 A1 | 10/2012 |

OTHER PUBLICATIONS

International Preliminary Report on Patentability (Forms PCT/IPEA/409 and PCT/IPEA/416) issued in PCT/JP2014/066371, dated Jun. 16, 2015.

International Search Report (Form PCT/ISA/210) issued in PCT/JP2014/066371, dated Aug. 12, 2014.

Japanese Office Action, dated Nov. 29, 2016, for Japanese Application No. 2013-155587, with English machine translation.

* cited by examiner

CIRCULAR POLARIZATION FILTER AND APPLICATION THEREFOR

CROSS-REFERENCE TO RELATED APPLICATIONS

This application is a continuation of PCT International Application No. PCT/JP2014/066371 filed on Jun. 20, 2014, which claims priorities under 35 U.S.C §119 (a) to Japanese Patent Applications Nos. 2013-130633 and 2013-155587 filed on Jun. 21 and Jul. 26, 2013, respectively, the entire contents of which are incorporated herein by reference.

BACKGROUND OF THE INVENTION

1. Field of the Invention

The present invention relates to a circular polarization filter. In addition, the present invention relates to the application of a circular polarization filter to a light source, a sensor, a sensor system, or the like.

2. Description of the Related Art

Circular polarization filters are filters capable of selectively transmitting or reflecting either right-handed circularly polarized light or left-handed circularly polarized light in a specific wavelength region, and are applied in various fields by utilizing characteristics of the obtained circularly polarized light.

For example, WO2012/144422A discloses usage of circularly polarized light in plant cultivation, and using a circular polarization plate in a lighting device for plant cultivation is described therein.

JP2013-36888A discloses an inspection system using circularly polarized light. JP2013-36888A discloses a technology of detecting cracks of a silicon substrate using a system which irradiates the silicon substrate with circularly polarized infrared light via a circular polarization filter and receives reflected or transmitted light from the silicon substrate via the circular polarization filter. This technology uses the fact that reflected or transmitted light from a portion having no cracks is circularly polarized light of the opposite sense and cannot be transmitted through the circular polarization filter, but in the case of reflected or transmitted light from a crack, light which can be detected via the circular polarization filter by diffuse reflection is generated.

SUMMARY OF THE INVENTION

An object of the invention is to provide a circular polarization filter capable of providing circularly polarized light with a high circular polarizance, or a circular polarization filter allowing an improvement in sensitivity in a sensor system using circularly polarized light. In addition, an object of the invention is to provide a high-sensitivity system as a sensor system using circularly polarized light.

The inventors of the invention have found that, during a trial-and-error process relating to a configuration in which the circular polarizance can be raised using a circular polarization filter using a layer having a cholesteric liquid crystalline phase fixed therein, the circular polarizance is significantly improved by employing a configuration in which the light transmitted through the layer having a cholesteric liquid crystalline phase fixed therein further passes via a transparent medium having a specific structure. The invention has been completed by further repeated studies based on this knowledge.

That is, the invention provides the following [1] to [16].

[1] A circular polarization filter including a circularly-polarized light separating layer having a cholesteric liquid crystalline phase fixed therein, in which the circularly-polarized light separating layer selectively transmits either right-handed circularly polarized light or left-handed circularly polarized light in a specific wavelength region, a transparent medium which is transparent with respect to light in the specific wavelength region is provided at least on one surface side of the circularly-polarized light separating layer, and the transparent medium has an inclined surface which forms an angle of 1° to 30° relative to the surface on the transparent medium side of the circularly-polarized light separating layer.

[2] The circular polarization filter according to [1], in which the circularly-polarized light separating layer is either a layer having a cholesteric liquid crystalline phase fixed therein or a laminate including a reflective linear polarizer and a λ/4 phase difference layer.

[3] The circular polarization filter according to [1] or [2], in which the transparent medium is directly brought into contact with or directly adhered to the circularly-polarized light separating layer.

[4] The circular polarization filter according to any one of [1] to [3], in which the transparent medium is a uniform medium.

[5] The circular polarization filter according to [4], in which the difference between a refractive index of the transparent medium and an average in-plane refractive index of the circularly-polarized light separating layer is not greater than 0.05.

[6] The circular polarization filter according to any one of [1] to [5], in which the inclined surface is an outermost surface.

[7] The circular polarization filter according to any one of [1] to [6], which has the transparent medium on both surfaces of the circularly-polarized light separating layer and has a uniform film thickness.

[8] The circular polarization filter according to any one of [1] to [7], in which the specific wavelength region is a wavelength region, having a width of at least 50 nm or greater, within a range of 800 nm to 1500 nm.

[9] The circular polarization filter according to any one of [1] to [8], further including a light blocking layer which blocks light in at least a part of a wavelength region excluding the specific wavelength region.

[10] The circular polarization filter according to [8], further including a light blocking layer which blocks light in a wavelength region, having a width of 50 nm or greater, within a range of 380 nm to 780 nm.

[11] A light source device including the circular polarization filter according to any one of [1] to [10], and a light source which emits light having a wavelength in the specific wavelength region.

[12] The light source device according to [11], in which the light source, the circularly-polarized light separating layer, and the transparent medium are disposed in this order.

[13] A sensor including the circular polarization filter according to any one of [1] to [10], and a light receiving element capable of detecting light having a wavelength in the specific wavelength region.

[14] The sensor according to [13], in which the light receiving element, the circularly-polarized light separating layer, and the transparent medium are disposed in this order.

[15] A sensor system including the circular polarization filter according to any one of [1] to [10], a light source which emits light having a wavelength in the specific wavelength region, and a light receiving element capable of detecting light having a wavelength in the specific wavelength region.

[16] The sensor system according to [15], in which the light source, the circularly-polarized light separating layer, and the transparent medium are disposed in this order, and the light receiving element, the circularly-polarized light separating layer, and the transparent medium are disposed in this order.

The invention provides a circular polarization filter capable of providing circularly polarized light with a high circular polarizance, and a circular polarization filter allowing an improvement in sensitivity in a sensor system using circularly polarized light. The circular polarization filter of the invention can be applied to plant cultivation or can be applied as a constituent member of a circular polarized light source device, a sensor, a sensor system, and the like.

DESCRIPTION OF THE PREFERRED EMBODIMENTS

Figure 1:
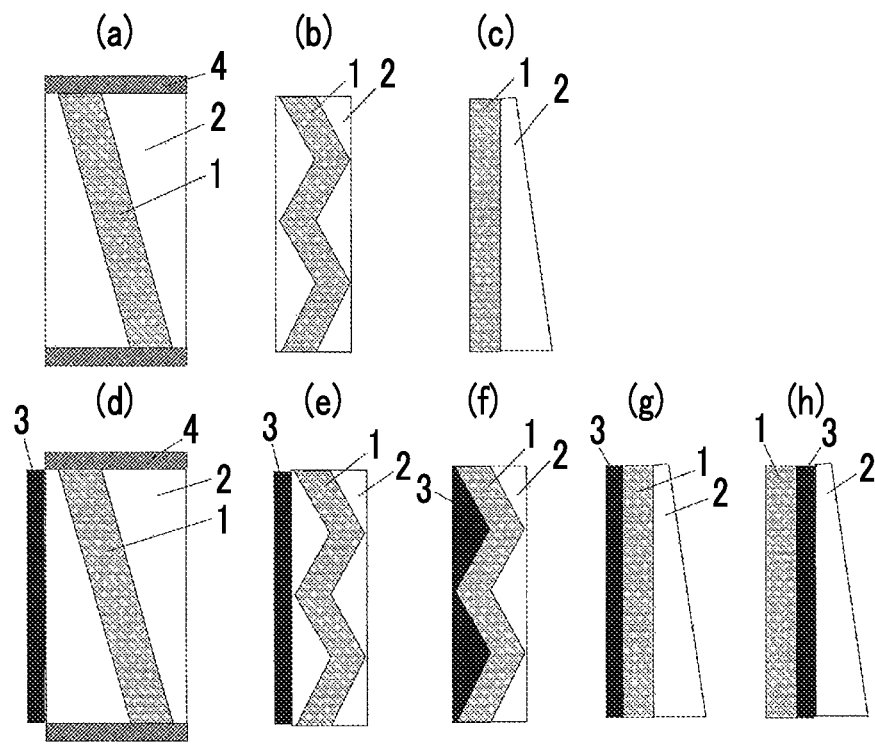
FIG. 1 shows examples (schematic sectional views) of a configuration of a circular polarization filter of the invention.

Hereinafter, the invention will be described in detail.

In this description, "~" is used in such a meaning that the numerical values described before and after "~" are included as a lower limit value and an upper limit value.

In this description, regarding circularly polarized light, the expression "selectively" is used in such a meaning that the light intensity of one of a right-handed circularly polarized light component and a left-handed circularly polarized light component of applied light is greater than that of the other circularly polarized light component. Specifically, when the expression "selectively" is used, the circular polarizance of light is preferably 0.3 or greater, more preferably 0.6 or greater, and even more preferably 0.8 or greater. Substantially, the circular polarizance of light is still more preferably 1.0.

Here, the circular polarizance is a value expressed by $|I_R-I_L|/(I_R+I_L)$ where $I_R$ denotes the intensity of a right-handed circularly polarized light component and $I_L$ denotes the intensity of a left-handed circularly polarized light component. In this description, the circular polarizance may be used to indicate a ratio of circularly polarized light components of light.

In this description, regarding circularly polarized light, the expression "sense" is used to mean either right-handed circularly polarized light or left-handed circularly polarized light. The sense of circularly polarized light is defined such that when light is viewed as it proceeds toward an observer, in the case in which a tip of an electric field vector rotates clockwise with an increase in time, the sense is right-handed circularly polarized light, and in the case in which it rotates counterclockwise, the sense is left-handed circularly polarized light.

In this description, the expression "sense" may also be used regarding the twisting direction of a helix of a cholesteric liquid crystal. As for the selective reflection by the cholesteric liquid crystal, when the twisting direction (sense) of the helix of the cholesteric liquid crystal is right-handed, right-handed circularly polarized light is reflected and left-handed circularly polarized light is transmitted, and when the sense is left-handed, left-handed circularly polarized light is reflected and right-handed circularly polarized light is transmitted.

In this description, the measurement of light intensity which is needed in relation to the calculation of light transmittance may be performed using, for example, a usual ultraviolet, visible, or near infrared spectrometer with the air as a reference.

The polarization state at each wavelength of light can be measured using a spectral radiance meter or a spectrometer having a circular polarization plate mounted thereon. In this case, the intensity of light measured through a right-handed circular polarization plate corresponds to $I_R$, and the intensity of light measured through a left-handed circular polarization plate corresponds to $I_L$. Furthermore, usual light sources such as incandescent light bulbs, mercury lamps, fluorescent lamps, and LEDs emit approximately natural light, and characteristics of producing polarized light of a circular polarization filter or a circularly-polarized light separating layer mounted thereon can be measured using, for example, a polarized light phase difference-analyzing apparatus "AXOSCAN" manufactured by Axometrics, Inc.

In addition, the measurement can also be performed by attaching a circular polarization filter to an illuminometer or an optical spectrometer. The ratio can be measured by attaching a right-handed circularly polarized light transmissive plate and measuring a right-handed circularly polarized light intensity and by attaching a left-handed circularly polarized light transmissive plate and measuring a left-handed circularly polarized light intensity.

(Circular Polarization Filter)

A circular polarization filter of the invention includes a circularly-polarized light separating layer and a transparent medium. If necessary, the circular polarization filter of the invention may include other layers or other constituent members. The circular polarization filter may have the transparent medium at least on one surface side of the circularly-polarized light separating layer. That is, the transparent medium may be positioned on one or both surface sides of the circularly-polarized light separating layer. In this description, regarding an object having a film form such as a layer or a filter, the expression "surface" is used to mean any of two surfaces showing a film area, and does not indicate a surface in a thickness direction unless particularly mentioned. The "surface" forms an angle with respect to a light incident direction in use of the circular polarization filter. For example, the above-described surface and the light incident direction may intersect at an angle of 30° to 90°.

The transparent medium is preferably a layer-shaped medium. The transparent medium positioned on one surface side of the circularly-polarized light separating layer is preferably a layer-shaped medium covering 50% or greater, 60% or greater, 70% or greater, 80% or greater, 90% or greater, 95% or greater, 96% or greater, 97% or greater, 98% or greater, or 99% or greater, and preferably and substantially 100% of the above one surface.

One surface of the circular polarization filter of the invention may be inclined or may not be inclined relative to the other surface. It is preferable that both surfaces of the circular polarization filter are not inclined with each other, that is, approximately parallel to each other, since the light entering from a normal direction of the circular polarization filter is emitted at an angle closer to the normal direction. The circular polarization filter of which both surfaces are approximately parallel to each other is preferred since the film thickness becomes uniform and good handleability is thus obtained. In this description, the expression "approximately parallel" is used to mean a relationship in which the angle formed between both surfaces is preferably less than 1*, 0.5° or less, 0.4° or less, 0.3° or less, 0.2° or less, 0.1° or less, 0.05° or less, 0.01° or less, or 0°.

FIG. 1 shows schematic sectional views (configurations viewed from a surface in a thickness direction) showing examples of a configuration of the circular polarization filter of the invention.

FIG. 1(a) shows an example in which transparent mediums are provided on both surfaces of a circularly-polarized light separating layer. Two transparent mediums having approximately the same shape are disposed on both surfaces of the circularly-polarized light separating layer such that two surfaces of the circular polarization filter are approximately parallel to each other. The configuration in which the transparent mediums are positioned on both surfaces of the circularly-polarized light separating layer is preferred as compared to, for example, a configuration in which a transparent medium is positioned on only one surface of a circularly-polarized light separating layer as shown in FIG. 1(c), since any surface may face a light source or a light receiving element during use and it is thus not necessary to perform orientation adjustment. Particularly, in sensors, a circular polarization filter having a configuration in which transparent mediums are positioned on both surfaces of a circularly-polarized light separating layer is preferred as a circular polarization filter which is used by being combined with a light receiving element.

As shown in FIG. 1(a), the circular polarization filter of the invention may have a light absorption layer on a surface in the thickness direction of the circular polarization filter. The light absorption layer positioned on the surface in the thickness direction of the circular polarization filter preferably absorbs light in a wavelength region including at least a controlled wavelength region. By providing the light absorption layer on the surface in the thickness direction, the influences of incident light from the thickness direction and reflected light from the surface in the thickness direction in the filter can be reduced, and circularly polarized light with a higher circular polarizance can be obtained.

FIG. 1(b) shows an example in which transparent mediums are provided on both surfaces of a circularly-polarized light separating layer, and the circularly-polarized light separating layer has a zigzag shape.

FIG. 1(c) shows an example in which a transparent medium is provided on one surface of a circularly-polarized light separating layer, and a structure in which one surface of a circular polarization filter is inclined relative to the other surface is provided. When using a circular polarization filter having the configuration of FIG. 1(c) in which a transparent medium is provided on one surface of a circularly-polarized light separating layer to cause circular polarization and separation and to obtain light with a higher circular polarizance, light (circularly polarized light, natural light, or unpolarized light) is preferably allowed to enter from the circularly-polarized light separating layer side. In sensor systems or the like, when it is necessary to selectively transmit and detect circularly polarized light of any sense, the circularly polarized light is preferably allowed to enter from the transparent medium side.

The light entering from a normal direction of the circularly-polarized light separating layer is refracted on the inclined surface which is an interface between the transparent medium and the air. In consideration of this optical path, if necessary, the position of a light source or the position of an object to be irradiated with circularly polarized light may be adjusted to further raise the circular polarizance.

FIGS. 1(d) to 1(h) show examples in which a light blocking layer is provided.

FIG. 1(d) shows an example in which a light blocking layer is added on one surface of the configuration of FIG. 1(a).

FIG. 1(e) shows an example in which a light blocking layer is added on one surface of the configuration of FIG. 1(b).

A circular polarization filter of FIG. 1(f) has a transparent medium on one surface of a circularly-polarized light separating layer having a zigzag shape, and has a light blocking layer on the other surface.

FIG. 1(g) shows an example in which a light blocking layer is added on one surface of the configuration of FIG. 1(c).

FIG. 1(h) shows an example in which a light blocking layer is added between the circularly-polarized light separating layer and the transparent medium of the configuration of FIG. 1(c).

(Optical Properties of Circular Polarization Filter)

The circular polarization filter is a filter which selectively transmits either right-handed circularly polarized light or left-handed circularly polarized light in a specific wavelength region. In this description, the specific wavelength region in which the circular polarization filter or the circularly-polarized light separating layer selectively transmits either right-handed circularly polarized light or left-handed circularly polarized light may be referred to as "controlled wavelength region".

The circular polarization filter may selectively transmit either right-handed circularly polarized light or left-handed circularly polarized light with respect to light in a specific wavelength region entering from any surface. The circular polarization filter may selectively transmit either right-handed circularly polarized light or left-handed circularly polarized light only with respect to light in a specific wavelength region entering from any one surface, and may not cause the same selective transmission as above with respect to light entering from the other surface.

The controlled wavelength region is not particularly limited. For example, it may be within a wavelength region of infrared rays, a wavelength region of visible light rays, or a wavelength region of ultraviolet rays, or may be a wavelength region extending across wavelength regions of infrared rays and visible light rays, wavelength regions of visible light rays and ultraviolet rays, or wavelength regions of infrared rays, visible light rays, and ultraviolet rays.

Infrared rays (infrared light) are electromagnetic waves in a wavelength region which is longer than that of visible light rays and shorter than that of radio waves. In general, near infrared rays are electromagnetic waves in a wavelength region of 700 nm to 2500 nm. Visible light rays are light rays having such a wavelength that these are seen by the human eye among electromagnetic waves, and indicate light in a wavelength region of 380 nm to 780 nm. Ultraviolet rays are electromagnetic waves in a wavelength region which is shorter than that of visible light rays and longer than that of X-rays. Ultraviolet rays may be light rays in a wavelength region which is distinguished from those of visible light rays and X-rays, and are, for example, light rays having a wavelength within a range of 10 nm to 420 nm.

The controlled wavelength region may be appropriately selected according to uses of the circular polarization filter. For example, in the case of use in a sensor system, a wavelength region corresponding to a wavelength region of near infrared light which is used in infrared cameras, infrared photoelectric sensors, infrared communication, or the like is selected. In the case of use in plant cultivation, a wavelength region desirable for a light source or sunlight to be used is selected.

The width of the controlled wavelength region is not particularly limited. For example, it may be a width including any one or more of wavelength regions of infrared rays, visible light rays, and ultraviolet rays, or be a wavelength width of 1 nm, 10 nm, 50 nm, 100 nm, 150 nm, or 200 nm. The width is preferably about 50 nm or greater.

In the circular polarization filter, in the controlled wavelength region, the light transmittance {(light intensity of transmitted circularly polarized light)/(light intensity of incident circularly polarized light)×100} of circularly polarized light of the same sense as incident light when either right-handed circularly polarized light or left-handed circularly polarized light is allowed to enter may be 70% or greater, 80% or greater, 90% or greater, 95% or greater, or 99% or greater, and preferably and substantially 100%. Simultaneously, in the same wavelength region, the light transmittance {(light intensity of transmitted circularly polarized light)/(light intensity of incident circularly polarized light)×100} of circularly polarized light of the same sense as incident light when circularly polarized light of the other sense is allowed to enter may be 30% or less, 20% or less, 10% or less, 5% or less, 1% or less, and preferably and substantially 0%.

Optical characteristics of the circular polarization filter with respect to light in a wavelength region other than the controlled wavelength region are not particularly limited, and preferred characteristics may be imparted according to uses. For example, when the circular polarization filter is used in a sensor system, the circular polarization filter preferably has low light transmittance in at least a part of a wavelength region other than the controlled wavelength region in some cases. The reason for this is because the light (light disturbing sensing) which reaches a light receiving element but is not required in sensing can be greatly reduced, a ratio of S to N can be increased, and thus the minimum light intensity which is detected by the light receiving element can be lowered. At this time, particularly in a wavelength region of the light which is not required in sensing, the average light transmittance may be 50% or less, 40% or less, 30% or less, 20% or less, 10% or less, or 5% or less.

It is preferable that in the circular polarization filter, the change in the refractive index is small in the normal direction and in a direction obliquely passing in the thickness direction of the circular polarization filter, and thus the traveling direction of the light does not change.

Hereinafter, the respective layers of the circular polarization filter will be described.

(Circularly-Polarized Light Separating Layer)

The circularly-polarized light separating layer has a function of selectively transmitting either right-handed circularly polarized light or left-handed circularly polarized light in a specific wavelength region. In addition, the circularly-polarized light separating layer can separate light (natural light, unpolarized light) in a specific wavelength region entering from one surface into right-handed circularly polarized light and left-handed circularly polarized light, and can selectively transmit any one of them to the other surface side.

By including the circularly-polarized light separating layer so as not to lose the above-described function of the circularly-polarized light separating layer due to other layers, the circular polarization filter has the function of selectively transmitting either right-handed circularly polarized light or left-handed circularly polarized light in a specific wavelength region. That is, for example, in the circular polarization filter, it is preferable that, by simultaneously including a circularly-polarized light separating layer which selectively transmits either right-handed circularly polarized light or left-handed circularly polarized light in a specific wavelength region and a circularly-polarized light separating layer which reflects circularly polarized light of the same sense in the same wavelength region, or by including a layer which reflects or absorbs light (natural light) in the same wavelength region on the optical path, the functions of the respective circularly-polarized light separating layers selectively transmitting either right-handed circularly polarized light or left-handed circularly polarized light are not offset.

The specific wavelength region (controlled wavelength region) in which the circularly-polarized light separating layer selectively transmits either right-handed circularly polarized light or left-handed circularly polarized light and the width thereof may be the same as in the above description of the circular polarization filter. The wavelength region in which the circularly-polarized light separating layer selectively transmits either right-handed circularly polarized light or left-handed circularly polarized light may include a wavelength region of light necessary according to the form of use of the circular polarization filter.

The circularly-polarized light separating layer may transmit, reflect, or absorb light in a wavelength region other than the wavelength region in which the circularly-polarized light separating layer selectively transmits either right-handed circularly polarized light or left-handed circularly polarized light.

As the circularly-polarized light separating layer, for example, a layer having a cholesteric liquid crystalline phase fixed therein or a laminate including a linearly-polarized light separating layer and a λ/4 phase difference layer may be used. When using a layer having a cholesteric liquid crystalline phase fixed therein as the circularly-polarized light separating layer, or when using a reflective linear polarizer as a linearly-polarized light separating layer of a laminate including the linearly-polarized light separating layer and a λ/4 phase difference layer, the circular polarization filter of the invention has particularly remarkable effects such as an improvement in the circular polarizance of circularly polarized light obtained due to the configuration of the invention.

(Layer Having Cholesteric Liquid Crystalline Phase Fixed Therein: Circularly-Polarized Light Separating Layer)

The cholesteric liquid crystalline phase is known to exhibit circularly polarized light-selective reflection to selectively reflect either right-handed circularly polarized light or left-handed circularly polarized light and to transmit the other circularly polarized light. In general, the cholesteric liquid crystal layer can selectively transmit either right-handed circularly polarized light or left-handed circularly polarized light with respect to the light entering from any surface, and can separate light into right-handed circularly polarized light and left-handed circularly polarized light even when the light enters from any surface, and selectively transmit any one of them to the other surface.

As a film having circularly polarized light-selective reflection properties, many films formed from a composition containing a polymerizable liquid crystal compound have been known, and prior art thereof can be referred to with respect to the layer having a cholesteric liquid crystalline phase fixed therein.

The layer having a cholesteric liquid crystalline phase fixed therein may be a layer in which the alignment of a liquid crystal compound having a cholesteric liquid crystalline phase is maintained. Typically, a polymerizable liquid crystal compound may be allowed to have an alignment state of the cholesteric liquid crystalline phase, and then polymerized and cured by ultraviolet irradiation, heating, or the like to form a layer having no fluidity, and the layer may be a layer changed to have such a state that the alignment form is not changed by an external field or external force. In the layer having a cholesteric liquid crystalline phase fixed therein, it is only necessary to maintain the optical properties of the cholesteric liquid crystalline phase in the layer, and the liquid crystalline compound in the layer may not exhibit liquid crystallinity. For example, the polymerizable liquid crystal compound may lose liquid crystallinity due to an increase in the molecular weight due to a hardening reaction.

In this description, the layer having a cholesteric liquid crystalline phase fixed therein may be referred to as a cholesteric liquid crystal layer or a liquid crystal layer.

The layer having a cholesteric liquid crystalline phase fixed therein exhibits circularly polarized light reflection derived from the helical structure of the cholesteric liquid crystal. A central wavelength $\lambda$ of the reflection depends on a pitch length P (period of helix) of the helical structure of the cholesteric phase, and satisfies the relationship of $\lambda=n\times p$ with an average refractive index n of the cholesteric liquid crystal layer. Thus, by adjusting the pitch length of the helical structure, the wavelength at which the circularly polarized light reflection is exhibited can be adjusted. That is, by adjusting the n value and the P value, the central wavelength $\lambda$ can be adjusted to be within a wavelength region of 780 nm to 1500 nm, and preferably 800 nm to 1500 nm in order to selectively transmit (reflect) either right-handed circularly polarized light or left-handed circularly polarized light in at least a part of the wavelength region of near infrared light, the central wavelength $\lambda$ can be adjusted to be within a wavelength region of 380 nm to 780 nm in order to selectively transmit (reflect) either right-handed circularly polarized light or left-handed circularly polarized light in at least a part of the wavelength region of visible light, and the central wavelength $\lambda$ can be adjusted to be within a wavelength region of 10 nm to 420 nm, and preferably 200 nm to 410 nm in order to selectively transmit (reflect) either right-handed circularly polarized light or left-handed circularly polarized light in at least a part of the wavelength region of ultraviolet light. The pitch length of the cholesteric liquid crystalline phase depends on the type of a chiral agent which is used with the polymerizable liquid crystal compound or the concentration of the chiral agent added. Accordingly, by adjusting these, a desired pitch length can be obtained. As a method of measuring helical sense or pitch, the methods described in "Introduction to Experimental Liquid Crystal Chemistry", edited by The Japanese Liquid Crystal Society, published in 2007 by Sigma Publishing Co., Ltd., p. 46, and "Liquid Crystal Handbook", the Editing Committee of Liquid Crystal Handbook, Maruzen Publishing Co., Ltd., p. 196 can be used.

The sense of circularly polarized light reflected from the cholesteric liquid crystal layer matches the helical sense. Therefore, a cholesteric liquid crystal layer in which the helical sense is either right-handed or left-handed may be used as the circularly-polarized light separating layer. The circularly-polarized light separating layer may be a laminate of two or more layers each having a cholesteric liquid crystalline phase fixed therein, but upon lamination, a plurality of cholesteric liquid crystal layers of the same helical sense with the same period P may be laminated. By laminating cholesteric liquid crystal layers of the same helical sense with the same period P, circular polarizing selectivity can be increased at a specific wavelength. Upon lamination, a cholesteric liquid crystal layer produced separately may be laminated using an adhesive or the like, but a process including: direct application of a liquid crystal composition containing a polymerizable liquid crystal compound and the like to a surface of the cholesteric liquid crystal layer formed through a method to be described later, alignment; and fixing is preferably repeated. By virtue of such a process, the alignment direction of liquid crystal molecules on the air interface side of the cholesteric liquid crystal layer formed in advance matches the alignment direction of liquid crystal molecules on the lower side of the cholesteric liquid crystal layer formed thereon, and the circularly-polarized light separating layer has good polarization characteristics.

A half band width $\Delta\lambda$ (nm) of a selective reflection band (circularly polarized light reflection band) in which circularly polarized light-selective reflection is exhibited depends on birefringence $\Delta n$ of the liquid crystal compound and the pitch length P, and satisfies the relationship of $\Delta\lambda=\Delta n\times P$. Consequently, a width of the selective reflection band can be controlled by adjusting $\Delta n$. $\Delta n$ can be adjusted by adjusting the type of the polymerizable liquid crystal compound or the mixing ratio thereof, or by controlling the temperature at the time of alignment fixing.

The width of the circularly polarized light reflection band (since the spectral profile of the circularly polarized light reflection of the cholesteric liquid crystal layer has a square shape, in general, the "width" is substantially the same as "half band width $\Delta\lambda$") is generally about 50 nm to 100 nm in a visible light region in one type of material. In order to widen the controlled wavelength region, two or more types of cholesteric liquid crystal layer with different periods P, which are different in the central wavelength of reflected light, may be laminated. In this case also, cholesteric liquid crystal layers of the same helical sense are preferably laminated.

In addition, in one cholesteric liquid crystal layer, the controlled wavelength region can also be widened by gradually changing the period P in the film thickness direction.

(Method of Producing Layer Having Cholesteric Liquid Crystalline Phase Fixed Therein)

Hereinafter, a material and a method for producing the cholesteric liquid crystal layer which can be used in the circularly-polarized light separating layer and in a light reflection layer to be described later will be described.

As a material which is used to form the cholesteric liquid crystal layer, a liquid crystal composition or the like containing a polymerizable liquid crystal compound and a chiral agent (optically active compound) can be exemplified. The liquid crystal composition further mixed with a surfactant, a polymerization initiator, or the like if necessary and dissolved in a solvent or the like is applied to a base (support, alignment film, cholesteric liquid crystal layer serving as underlying layer, or the like), and after cholesteric alignment and maturing, fixing is performed, and thus the cholesteric liquid crystal layer can be formed.

Polymerizable Liquid Crystal Compound

The polymerizable liquid crystal compound may be either a rod-shaped liquid crystal compound or a discotic liquid crystal compound, but a rod-shaped liquid crystal compound is preferred.

Examples of the rod-shaped polymerizable liquid crystal compound which forms the cholesteric liquid crystal layer include a rod-shaped nematic liquid crystal compound. As the rod-shaped nematic liquid crystal compound, azomethines, azoxys, cyanobiphenyls, cyanophenyl esters, benzoate esters, phenyl cyclohexanecarboxylate esters, cyanophenylcyclohexanes, cyano-substituted phenylpyrimidines, alkoxy-substituted phenylpyrimidines, phenyldioxanes, tolanes, and alkenylcyclohexylbenzonitriles are preferably used. Not only low molecular liquid crystal compounds, but also high molecular liquid crystal compounds are usable here.

The polymerizable liquid crystal compound is obtained by introducing a polymerizable group into a liquid crystal compound. Examples of the polymerizable group include an unsaturated polymerizable group, an epoxy group, and an aziridinyl group. An unsaturated polymerizable group is preferred, and an ethylenic unsaturated polymerizable group is more preferred. The polymerizable group can be introduced into the molecule of the liquid crystal compound by various methods. The number of the polymerizable groups of the polymerizable liquid crystal compound is preferably 1 to 6, and more preferably 1 to 3. Examples of the polymerizable liquid crystal compound include the compounds described in Makromol. Chem., Vol. 190, p. 2255 (1989), Advanced Materials, Vol. 5, p. 107 (1993), U.S. Pat. No. 4,683,327A, U.S. Pat. No. 5,622,648A, and U.S. Pat. No. 5,770,107A, WO95/22586A, WO95/24455A, WO97/00600A, WO98/23580A, WO98/52905A, JP1989-272551A (JP-H1-272551A), JP1994-16616A (JP-H6-16616A), JP1995-110469A (JP-H7-110469A), JP1999-80081A (JP-H11-80081A), and JP2001-328973A. Two or more types of polymerizable liquid crystal compound may be used in combination. When two or more types of polymerizable liquid crystal compound are used in combination, the alignment temperature can be reduced.

The amount of the polymerizable liquid crystal compound added in the liquid crystal composition is preferably 80 mass % to 99.9 mass %, more preferably 85 mass % to 99.5 mass %, and even more preferably 90 mass % to 99 mass % with respect to the mass of the solid content (mass excluding mass of solvent) of the liquid crystal composition.

Chiral Agent (Optically Active Compound)

The chiral agent has a function of inducing the helical structure of the cholesteric liquid crystalline phase. A chiral compound may be selected according to the purpose since the sense of the helix or the pitch of the helix to be induced differs depending on the compound.

The chiral agent is not particularly limited, and a known compound (for example, those described in Liquid Crystal Device Handbook, Chap. 3, Section 4-3, Chiral Agent for TN, STN, p. 199, edited by Japan Society for the Promotion of Science, No. 142 Committee, 1989), isosorbide, or an isomannide derivative can be used.

The chiral agent generally contains an asymmetric carbon atom, but an axially asymmetric compound or a planarly asymmetric compound which does not contain an asymmetric carbon atom can also be used as the chiral agent. Examples of the axially asymmetric compound or planarly asymmetric compound include binaphthyl, helicene, paracyclophane, and derivatives thereof. The chiral agent may have a polymerizable group. When both of the chiral agent and the liquid crystal compound have a polymerizable group, a polymer having a repeating unit induced from the polymerizable liquid crystal compound and a repeating unit induced from the chiral agent can be formed by a polymerization reaction of the polymerizable chiral agent and the polymerizable liquid crystal compound. In this aspect, the polymerizable group of the polymerizable chiral agent is preferably the same kind of group as the polymerizable group of the polymerizable liquid crystal compound. Accordingly, the polymerizable group of the chiral agent is also preferably an unsaturated polymerizable group, an epoxy group, or an aziridinyl group, more preferably an unsaturated polymerizable group, and particularly preferably an ethylenically unsaturated polymerizable group.

The chiral agent may be a liquid crystal compound.

The chiral agent preferably has a photoisomerization group since a desired reflection wavelength pattern corresponding to an emission wavelength can be formed by application and alignment, followed by photomask irradiation with active rays or the like. As the photoisomerization group, an isomerization site of a compound exhibiting photochromic properties, an azo group, an azoxy group, and a cinnamoyl group are preferred. As a specific compound, a compound described in JP2002-80478A, JP2002-80851A, JP2002-179668A, JP2002-179669A, JP2002-179670A, JP2002-179681A, JP2002-179682A, JP2002-338575A, JP2002-338668A, JP2003-313189A, or JP2003-313292A can be used.

The content of the chiral agent in the liquid crystal composition is preferably 0.01 mol % to 200 mol %, and more preferably 1 mol % to 30 mol % of the amount of the polymerizable liquid crystalline compound.

Polymerization Initiator

The liquid crystal composition preferably contains a polymerization initiator. In an aspect in which the polymerization reaction is allowed to proceed by ultraviolet irradiation, the polymerization initiator to be used is preferably a photopolymerization initiator capable of initiating a polymerization reaction by ultraviolet irradiation. Examples of the photopolymerization initiator include α-carbonyl compounds (described in U.S. Pat. No. 2,367,661A and U.S. Pat. No. 2,367,670A), acyloin ethers (described in U.S. Pat. No. 2,448,828A), α-hydrocarbon-substituted aromatic acyloin compounds (described in U.S. Pat. No. 2,722,512A), polynuclear quinone compounds (described in U.S. Pat. No. 3,046,127A and U.S. Pat. No. 2,951,758A), a combination of triarylimidazole dimer and p-aminophenyl ketone (described in U.S. Pat. No. 3,549,367A), acridine and phenazine compounds (described in JP1985-105667A (JP-S60-105667A) and U.S. Pat. No. 4,239,850A), and oxadiazole compounds (described in U.S. Pat. No. 4,212,970A).

The content of the photopolymerization initiator in the liquid crystal composition is preferably 0.1 mass % to 20 mass %, and more preferably 0.5 mass % to 5 mass % with respect to the content of the polymerizable liquid crystal compound.

Crosslinking Agent

The liquid crystal composition may arbitrarily contain a crosslinking agent to improve film strength and durability after curing. As the crosslinking agent, a crosslinking agent which is cured by ultraviolet rays, heat, humidity, or the like can be suitably used.

The crosslinking agent is not particularly limited, and can be appropriately selected according to the purpose. Examples thereof include polyfunctional acrylate compounds such as trimethylolpropane tri(meth)acrylate and pentaerythritol tri(meth)acrylate; epoxy compounds such as glycidyl(meth)acrylate and ethylene glycol diglycidyl ether; aziridine compounds such as 2,2-bishydroxymethylbutanol-tris[3-(1-aziridinyl)propionate] and 4,4-bis(ethyleneiminocarbonylamino)diphenylmethane; isocyanate compounds such as hexamethylene diisocyanate and biuret-type isocyanate; polyoxazoline compounds having an oxazoline group on a side chain; and alkoxysilane compounds such as vinyltrimethoxysilane and N-(2-aminoethyl)3-aminopropyltrimethoxysilane. Furthermore, a known catalyst can be used according to the reactivity of the crosslinking agent, and productivity can be improved along with the improvement in film strength and durability. These may be used alone or in combination of two or more kinds thereof.

The content of the crosslinking agent is preferably 3 mass % to 20 mass %, and more preferably 5 mass % to 15 mass %. When the content of the crosslinking agent is less than 3 mass %, the crosslinking density improving effect may not be obtained, and when the content is greater than 20% by mass, stability of the cholesteric liquid crystal layer may be reduced.

Alignment Control Agent

An alignment control agent which contributes to stably or rapidly forming a planar-aligned cholesteric liquid crystal layer may be added to the liquid crystal composition. Examples of the alignment control agent include fluoro (meth)acrylate polymers described in paragraphs [0018] to [0043] of JP2007-272185A and compounds expressed by Formulae (I) to (IV) described in paragraphs [0031] to [0034] of JP2012-203237A.

The alignment control agents may be used alone or in combination of two or more kinds thereof.

The amount of the alignment control agent added in the liquid crystal composition is preferably 0.01 mass % to 10 mass %, more preferably 0.01 mass % to 5 mass %, and particularly preferably 0.02 mass % to 1 mass % with respect to the total mass of the polymerizable liquid crystal compound.

Other Additives

The liquid crystal composition may contain at least one selected from various additives such as a surfactant for adjusting surface tension of the coating film and for uniformizing the film thickness and a polymerizable monomer. In the liquid crystal composition, if necessary, a polymerization inhibitor, an antioxidant, an ultraviolet absorber, a light stabilizer, a coloring material, fine metal oxide particles, and the like can be further added within such a range that the optical properties are not reduced.

A liquid crystal composition which is obtained by dissolving a polymerizable liquid crystal compound and a polymerization initiator, and if necessary, a chiral agent, a surfactant, and the like in a solvent is applied to a base and dried to obtain a coating film, the coating film is irradiated with active rays to polymerize the cholesteric liquid crystal composition, and thus a cholesteric liquid crystal layer in which cholesteric regularity is fixed can be formed. In addition, a laminate film consisting of a plurality of cholesteric liquid crystal layers can be formed by repeating the process of manufacturing a cholesteric liquid crystal layer.

The solvent used to prepare the liquid crystal composition is not particularly limited, and can be appropriately selected according to the purpose. An organic solvent is preferably used.

The organic solvent is not particularly limited, and can be appropriately selected according to the purpose. Examples thereof include ketones, alkyl halides, amides, sulfoxides, heterocyclic compounds, hydrocarbons, esters, and ethers. These may be used alone or in combination of two or more kinds thereof. Among these, when environmental load is taken into consideration, ketones are particularly preferred.

The method of applying the liquid crystal composition to the base is not particularly limited, and can be appropriately selected according to the purpose. Examples thereof include a wire bar coating method, a curtain coating method, an extrusion coating method, a direct gravure coating method, a reverse gravure coating method, a die coating method, a spin coating method, a dip coating method, a spray coating method, and a slide coating method. Furthermore, the application can also be performed by transferring the liquid crystal composition, which has been separately coated on a support, to the base. By heating the applied cholesteric liquid crystal composition, liquid crystal molecules are aligned. The heating temperature is preferably 200° C. or lower, and more preferably 130° C. or lower. Through this alignment treatment, an optical thin film in which the polymerizable liquid crystal compound is twist-aligned to have a helical axis in a direction substantially perpendicular to the film surface is obtained.

The aligned liquid crystal compound may be further polymerized. For the polymerization, any of thermal polymerization and photopolymerization by light irradiation may be performed, but photopolymerization is preferred. For the light irradiation, ultraviolet rays are preferably used. The irradiation energy is preferably 20 mJ/cm$^2$ to 50 J/cm$^2$, and more preferably 100 mJ/cm$^2$ to 1500 mJ/cm$^2$. In order to accelerate the photopolymerization reaction, light irradiation may be performed during heating or under a nitrogen atmosphere. The wavelength of ultraviolet rays for irradiation is preferably 350 nm to 430 nm. From the viewpoint of stability, the higher the polymerization reaction rate, the better. The rate is preferably 70% or higher, and more preferably 80% or higher.

The polymerization reaction rate can be determined by measuring a proportion of the consumed polymerizable functional groups by using an IR absorption spectrum.

The thickness of the circularly-polarized light separating layer is preferably 1 μm to 150 μm, more preferably 2 μm to 100 μm, and even more preferably 3 μm to 50 μm.

(Laminate Including Linearly-Polarized Light Separating Layer and λ/4 Phase Difference Layer: Circularly-Polarized Light Separating Layer)

In the circularly-polarized light separating layer formed of a laminate including a linearly-polarized light separating layer and a λ/4 phase difference layer, light entering from a surface of the linearly-polarized light separating layer is changed into linearly polarized light by reflection or absorption, and then changed into right- or left-handed circularly polarized light by passing through the λ/4 phase difference layer. In the case of light incidence from the λ/4 phase difference layer, light in any polarization state is changed into linearly polarized light by the linearly-polarized light separating layer through which the light passes finally, but particularly, when the incident light is circularly polarized light, the light is changed into linearly polarized light parallel or perpendicular to the transmission axis of the linearly-polarized light separating layer by the λ/4 phase difference layer. Accordingly, light is preferably allowed to enter from the side of the λ/4 phase difference layer in order to use it in discrimination of the sense of the incident circularly polarized light, and light is preferably allowed to enter from the side of the linearly-polarized light separating layer when using emitted circularly polarized light.

A linear polarizer corresponding to the above-described controlled wavelength region may be used as the linearly-polarized light separating layer.

Linear Polarizer

As described above, in the circular polarization filter of the invention, the circular polarizance of circularly polarized light obtained particularly when a laminate including a reflective linearly-polarized light separating layer and a $\lambda/4$ phase difference layer is used as the circularly-polarized light separating layer is significantly improved. Accordingly, as the linear polarizer, a reflective linear polarizer is preferred.

Examples of the reflective linear polarizer (linearly polarized light reflection plate) include (i) a linearly polarized light reflection plate having a multi-layer structure, (ii) a polarizer including a laminate of thin films having different types of birefringence, (iii) a wire grid-type polarizer, (vi) a polarizing prism, and (v) a scattering anisotropic polarizing plate.

As (i) the linearly polarized light reflection plate having a multi-layer structure, a laminate of a plurality of dielectric thin films having different refractive indices can be exemplified. In order to form a wavelength-selective reflection film, it is preferable that a dielectric thin film having a high refractive index and a dielectric thin film having a low refractive index are alternately laminated in a plurality of layers. However, the number of film types is not limited to two, and three or more types of film may be used.

The number of the layers to be laminated is preferably 2 to 20, more preferably 2 to 12, even more preferably 4 to 10, and particularly preferably 6 to 8. When the number of the layers to be laminated is greater than 20, production efficiency may decrease due to multi-layer vapor deposition.

The order of laminating the dielectric thin films is not particularly limited, and can be appropriately selected according to the purpose. For example, when the refractive indices of the adjacent films are high, a film having a lower refractive index is laminated first. Inversely, when the refractive indices of the adjacent films are low, a film having a higher refractive index is laminated first. The refractive index is determined to be high or low based on a refractive index of 1.8. The criterion for determining whether a refractive index is high or low is not absolute. Among materials having a high refractive index, there may be materials having a relatively high refractive index and materials having a relatively low refractive index, and these may be alternately used.

Examples of the material of the dielectric thin film having a high refractive index include $Sb_2O_3$, $Sb_2S_3$, $Bi_2O_3$, $CeO_2$, $CeF_3$, $HfO_2$, $La_2O_3$, $Nd_2O_3$, $Pr_6O_{11}$, $Sc_2O_3$, $SiO$, $Ta_2O_5$, $TiO_2$, $TlCl$, $Y_2O_3$, $ZnSe$, $ZnS$, and $ZrO_2$. Among these, $Bi_2O_3$, $CeO_2$, $CeF_3$, $HfO_2$, $SiO$, $Ta_2O_5$, $TiO_2$, $Y_2O_3$, $ZnSe$, $ZnS$, and $ZrO_2$ are preferred, and among these, $SiO$, $Ta_2O_5$, $TiO_2$, $Y_2O_3$, $ZnSe$, $ZnS$, and $ZrO_2$ are particularly preferred.

Examples of the material of the dielectric thin film having a low refractive index include $Al_2O_3$, $BiF_3$, $CaF_2$, $LaF_3$, $PbCl_2$, $PbF_2$, $LiF$, $MgF_2$, $MgO$, $NdF_3$, $SiO_2$, $Si_2O_3$, $NaF$, $ThO_2$, and $ThF_4$. Among these, $Al_2O_3$, $BiF_3$, $CaF_2$, $MgF_2$, $MgO$, $SiO_2$, and $Si_2O_3$ are preferred, and $Al_2O_3$, $CaF_2$, $MgF_2$, $MgO$, $SiO_2$, and $Si_2O_3$ are particularly preferred.

The material of the dielectric thin film is not particularly limited in terms of the atomic ratio, and can be appropriately selected according to the purpose. If the concentration of the atmospheric gas at the time of film formation is varied, the atomic ratio can be adjusted.

The method of forming the dielectric thin film is not particularly limited, and can be appropriately selected according to the purpose. Examples thereof include physical vapor deposition methods (PVD methods) such as ion plating, vacuum vapor deposition using ion beams, and sputtering, and chemical vapor deposition methods (CVD methods). Among these, a vacuum vapor deposition method and a sputtering method are preferred, and a sputtering method is particularly preferred.

As the sputtering method, a DC sputtering method with a high film forming rate is preferred. Moreover, in the DC sputtering method, materials having high conductivity are preferably used.

In addition, examples of the method of forming a multi-layer film through the sputtering method include (1) a 1-chamber method in which films are formed alternately or sequentially from a plurality of targets in a single chamber and (2) a multi-chamber method in which films are continuously formed in a plurality of chambers. Among these, a multi-chamber method is particularly preferred from the viewpoint of productivity and prevention of contamination of the materials.

The thickness of the dielectric thin film is preferably $\lambda/16$ to $\lambda$, more preferably $\lambda/8$ to $3\lambda/4$, and even more preferably $\lambda/6$ to $3\lambda/8$ in order of optical wavelength.

Some light rays propagated in the vapor-deposited dielectric layer undergo multiple reflection for each dielectric thin film. Due to interference of the reflected light rays, only the light having a wavelength which is determined by a product of the thickness of the dielectric thin film and the optical refractive index of the film is selectively transmitted through the vapor-deposited dielectric layer. A central transmission wavelength of the vapor-deposited dielectric layer has angle dependency with respect to the incident light, and when the incident light is varied, the transmission wavelength can be changed.

As (ii) the polarizer including a laminate of thin films having different types of birefringence, for example, a polarizer described in JP1997-506837A (JP-H9-506837A) or the like can be used.

Specifically, when processing is performed under conditions selected to obtain a refractive index relationship, it is possible to form a polarizer by using a wide variety of materials. In general, one of first materials needs to have a refractive index different from that of a second material in the selected direction. The difference in the refractive index can be achieved by various methods including stretching during or after film formation, extrusion molding, and coating. Moreover, in order to subject two materials to extrusion simultaneously, the materials preferably have similar rheological properties (for example, melt viscosity).

As the polarizer including a laminate of thin films having different types of birefringence, commercially available products can be used, and examples thereof include DBEF (trade name) manufactured by 3M Company.

(iii) The wire grid-type polarizer is a polarizer which transmits one component of polarized light and reflects the other component thereof by birefringence of fine metal wires.

The wire grid polarizer is obtained by periodically arranging metal wires, and is used as a polarizer mainly in a terahertz wavelength band. In order to allow the wire grids to function as a polarizer, it is necessary for the interval between wires to be sufficiently smaller than the wavelength of the incident electromagnetic waves.

In the wire grid polarizer, metal wires are arranged at the same intervals. A polarized light component in a polarization direction parallel to a longitudinal direction of the metal wires is reflected from the wire grid polarizer, and a polarized light component in a polarization direction perpendicular thereto is transmitted through the wire grid polarizer.

As the wire grid-type polarizer, commercially available products can be used, and examples of the commercially available products include a wire grid polarization filter 50×50, NT46-636, manufactured by Edmund Optics Inc.

The thickness of the linearly-polarized light separating layer is preferably 0.05 µm to 300 µm, more preferably 0.2 µm to 150 µm, and even more preferably 0.5 µm to 100 µm.

(λ/4 Phase Difference Layer)

The front phase difference of the λ/4 phase difference plate preferably has a length of ¼ of a wavelength (preferably central wavelength) (for example, central wavelength of emission wavelengths of a light source when the filter is used in a light source device) in the controlled wavelength region, or is "central wavelength*n±¼ of central wavelength (n is an integer)". For example, when the central wavelength of the emitted light of the light source is 1000 nm, a phase difference of 250 nm, 750 nm, 1250 nm, 1750 nm, or the like is preferred. In addition, the smaller the dependence of the phase difference on the light incidence angle, the better. In view of this, a phase difference plate having a phase difference having a length of ¼ of the central wavelength is most preferred.

The front phase difference can be measured by allowing light having a wavelength in the controlled wavelength region to enter in a normal direction of the film in a KOBRA 21ADH or WR (manufactured by Oji Scientific Instruments). When selecting a measurement wavelength, a wavelength-selective filter is manually exchanged or a measurement value is converted using a program or the like to perform the measurement.

The λ/4 wave plate is not particularly limited, and can be appropriately selected according to the purpose. Examples thereof include a stretched polycarbonate film, a stretched norbornene polymer film, a transparent film in which inorganic particles having birefringence such as strontium carbonate are contained and aligned, and a thin film obtained by obliquely depositing an inorganic dielectric on a support. In addition, examples of the λ/4 wave plate include (1) a phase difference plate in which a birefringent film having large retardation and a birefringent film having small retardation are laminated such that optical axes thereof are perpendicular to each other as described in JP1993-27118A (JP-H5-27118A) and JP1993-27119A (JP-H5-27119), (2) a phase difference plate in which a polymer film which gives a λ/4 wavelength at a specific wavelength and a polymer film which is made of the same material and gives a λ/2 wavelength at the same wavelength are laminated to obtain a λ/4 wavelength in a wide wavelength region as described in JP1998-68816A (JP-H10-68816A), (3) a phase difference plate which is capable of achieving a λ/4 wavelength in a wide wavelength region by laminating two polymer films as described in JP1998-90521A (JP-H10-90521A), (4) a phase difference plate which uses a modified polycarbonate film and is capable of achieving a λ/4 wavelength in a wide wavelength region as described in WO00/26705A, and (5) a phase difference plate which uses a cellulose acetate film and is capable of achieving a λ/4 wavelength in a wide wavelength region as described in WO00/65384A.

As such a λ/4 wave plate, commercially available products can be used, and examples thereof include Pureace WR (trade name) (manufactured by Teijin Limited).

The circularly-polarized light separating layer can be produced by sticking the linear polarizer and the λ/4 wave plate together such that the angle of the optical axis of the λ/4 wave plate relative to the polarization absorption axis of the linear polarization plate is 45 degrees. Examples of the sticking method include a method of performing lamination of rolls using an adhesive film. When this circular polarization plate is mounted on an emission light source, the linear polarization plate is disposed and used so as to be a surface closer to the light source, and thus polarized light conversion to circularly polarized light can be performed.

The above-described phase difference plate can also be used to widen the controlled wavelength region of the circular polarization filter of the invention, but a wide band phase difference plate is more preferably used. The wide band phase difference plate is a phase difference plate in which a phase difference angle is constant over a wide wavelength range, and examples thereof include a laminated phase difference plate which covers a wide band by laminating phase difference layers which are different in the wavelength dispersion of a birefringence index such that slow axes thereof are perpendicular to each other, a high molecular film which is formed by aligning substituents which are different in the wavelength dispersion of a birefringence index such that arrangement axes thereof are perpendicular to each other using the above principle at a molecular level, and a phase difference plate in which a layer with a phase difference of λ/2 and a layer with a phase difference of λ/4 with respect to a wavelength (λ) of a wavelength region used are laminated such that slow axes thereof intersect at 60 degrees.

The thickness of the λ/4 layer is preferably 0.2 µm to 300 µm, more preferably 0.5 µm to 150 µm, and even more preferably 1 µm to 80 µm.

(Transparent Medium)

The transparent medium is characterized in that it has an inclined surface which forms an angle of 10 to 30° relative to a surface on the transparent medium side of the circularly-polarized light separating layer. The inventors of the invention have accidentally found that the circular polarizance of circularly polarized light obtained by transmission through the circularly-polarized light separating layer formed of a cholesteric liquid crystal layer significantly increases by further transmission through the transparent medium having an inclined surface in addition to the circularly-polarized light separating layer. In addition, the inventors of the invention have further repeated studies and found that the inclination thereof is preferably 1° to 30° relative to the surface on the transparent medium side of the circularly-polarized light separating layer. In this description, forming an angle of 1° to 30° may be used in such a meaning that there is a portion in which the surfaces intersect and an angle of 1° to 30° is formed therebetween in the circular polarization filter, or that when extended surfaces including the surfaces are assumed, the angle formed by intersection of the extended surfaces is 1° to 30°. The angle may be 1° to 30°, preferably 4° to 15°, and more preferably about 10°.

In this description, the angle, that is, the angle formed between the surface on the transparent medium side of the circularly-polarized light separating layer and the inclined surface is referred to as "inclination angle". In addition, in this description, the term "inclination direction" may be used. The term "inclination direction" indicates which direction in the surface on the transparent medium side of the circularly-polarized light separating layer the inclined surface is inclined to form an angle. The inclination direction of the inclined surface of the circular polarization filter of the invention is not particularly limited.

In the inclination, the inclination direction and the inclination angle may be continuous in the whole surface of the circular polarization filter as shown in FIGS. 1(a), 1(c), 1(d), 1(g), and 1(h), or as shown in FIGS. 1(b), 1(e), and 1(f), the inclination direction may be discontinuous and surfaces having different inclination directions may alternately exist. At this time, the widths of the alternately existing inclinations are not particularly limited. These may be 100 µm to 20 mm, and preferably 200 µm to 5 mm. When the width is less than 100 µm, the light transmittance may be reduced by a diffraction effect. Moreover, the inclination angles of the alternately existing inclinations may be the same as or different from each other.

In the inclination, the inclination direction is continuous, that is, the inclination direction is the same in the whole surface of the inclined surface. However, the inclination angle may be discontinuous, that is, may change.

In the circular polarization filter of the invention, the inclined surface is preferably an outermost surface.

In the controlled wavelength region, the transparent medium may be transparent. That is, in the controlled wavelength region, the light transmittance of the transparent medium may be 50% or greater, 60% or greater, 70% or greater, 80% or greater, 90% or greater, 95% or greater, 99% or greater, or substantially 100%. The light transmittance of the transparent medium may be high or low in a wavelength region other than the specific wavelength region.

The difference in the average refractive index (average in-plane refractive index) between the transparent medium and the circularly-polarized light separating layer in the controlled wavelength region is preferably small. Specifically, the difference may be not greater than 0.2, not greater than 0.1, or not greater than 0.05. In general, the circularly-polarized light separating layer formed of a cholesteric liquid crystal layer has an average refractive index of about 1.55 to 1.6. Accordingly, the refractive index of the transparent medium may be within a range of, for example, 1.3 to 1.8, and preferably 1.4 to 1.7.

Regarding the average refractive index, values in the catalog of various optical films, Polymer Handbook (John Wiley & Sons, Inc.), can be used. A material of which the average refractive index value is not known can be subjected to the measurement using an Abbe's refractometer. Average refractive index values of major optical films are exemplified as follows: cellulose acylate (1.48), cycloolefin polymer (1.52), polycarbonate (1.59), polymethyl methacrylate (1.49), and polystyrene (1.59). The refractive index of glass is about 1.51.

The transparent medium may be formed of one uniform medium or a plurality of mediums.

Examples of the transparent medium formed of one uniform medium include a glass plate and a plastic plate. Specific examples of the material of the transparent medium include glass, polymers such as polystyrene, polymethyl methacrylate resin, fluororesin, polyethylene, polycarbonate, acrylic resin, polyester, epoxy resin, polyurethane, polyamide, polyolefin, cellulose derivatives, and silicone (including modified silicone such as silicone polyurea), and a material having an acrylic monomer, epoxy, or oxetane monomer polymerized and fixed therein.

Examples of the transparent medium formed of a plurality of mediums include a medium having a configuration provided with a layer formed from a composition (polymer composition or polymerizable composition to be polymerized and fixed) applied to be inclined to a flat glass plate or plastic film, a medium which is formed by introducing a composition having fluidity between two flat glass plates or plastic films, and a laminate of a plurality of transparent films. As the material of the respective mediums in the transparent medium formed of the plurality of mediums, for example, the materials exemplified as an example of the transparent medium formed of one uniform medium can be used.

A light blocking layer, an alignment layer, an adhesion layer, a support, and the like to be described later may configure a part or the whole of the transparent medium.

A substance having such a refractive index that the difference between the refractive index and the average refractive index of the circularly-polarized light separating layer is large is preferably not included between the surface on the transparent medium side of the circularly-polarized light separating layer and the inclined surface of the transparent medium. In other words, a substance which greatly changes the proceeding direction of the light transmitted through the circular polarization filter is preferably not included between the surface on the transparent medium side of the circularly-polarized light separating layer and the inclined surface of the transparent medium in the form of greatly changing the proceeding direction of the light Particularly, a layer having such a refractive index that the difference between the refractive index and the average refractive index of the circularly-polarized light separating layer is large is preferably not included on the optical path of the circular polarization filter. For example, a substance having such a refractive index that the difference between the refractive index and the average refractive index of the circularly-polarized light separating layer is greater than 0.2, greater than 0.1, or greater than 0.05 is preferably not included. A gas medium such as the air is preferably substantially not included between the surface on the transparent medium side of the circularly-polarized light separating layer and the inclined surface. The reason for this is that the difference between the refractive index of a gas phase and the average refractive index of the circularly-polarized light separating layer is large. Furthermore, only the transparent medium, or only the transparent medium and an adhesion layer for adhesion between the circularly-polarized light separating layer and the transparent medium preferably exist between the surface on the transparent medium side of the circularly-polarized light separating layer and the inclined surface of the transparent medium. That is, the transparent medium is preferably directly brought into contact with or directly adhered to the circularly-polarized light separating layer.

(Light Blocking Layer)

The circular polarization filter may include a light blocking layer. The light blocking layer functions such that light in a wavelength region other than the specific wavelength region in which the circular polarization filter selectively transmits either right-handed circularly polarized light or left-handed circularly polarized light is not transmitted through the filter. The light blocking layer preferably blocks natural light. In addition, the light blocking layer preferably blocks all of unpolarized light, circularly polarized light, and linear polarized light. Examples of the light blocking layer include a light reflection layer and a light absorption layer.

The width of the light wavelength region in which the light blocking layer reflects or absorbs light is not particularly limited, and may be 10 nm or greater, 20 nm or greater, 30 nm or greater, 40 nm or greater, or 50 nm or greater. The light wavelength region in which light is reflected or absorbed by the blocking layer preferably includes a wavelength region of unnecessary light for uses of the circular polarization filter. For example, when the filter is used in a sensor, a wavelength region in which unnecessary light for sensing (light interfering with sensing) is easily detected is preferably included.

Similarly to the transparent medium, the difference between the refractive index of the light blocking layer and the average refractive index (average in-plane refractive index) of the circularly-polarized light separating layer in the controlled wavelength region is preferably small.

In the case of a circular polarization filter used in a sensor system, the light blocking layer may have high light reflection properties or high light absorbability in at least a part of a wavelength region excluding a detection wavelength region of a sensor (light receiving element) to be used. Otherwise, the light blocking layer may have high light reflection properties or high light absorbability in at least a part of a wavelength region excluding an emission wavelength region of a light source to be used or a light receiving region of a light receiving element.

For example, in a sensor system, when using circularly polarized light in a near infrared region, a light blocking layer having high light reflection properties or high light absorbability in at least a part of a visible light region may be used. Since silicon photodiodes which are generally used as a light receiving element (light detector) exist most frequently in the usage environment and have sensitivity up to the visible light region which is a main cause of noise, the light blocking layer preferably performs light reflection or absorption centering on the visible light region. In addition, the visible light blocking layer preferably substantially reflects or absorbs light in a wavelength region of near infrared light in which the circularly-polarized light separating layer selectively transmits either right-handed circularly polarized light or left-handed circularly polarized light.

The thickness of the light blocking layer is preferably 2 μm to 500 μm, more preferably 5 μm to 300 μm, and even more preferably 10 μm to 150 μm.

Hereinafter, the light reflection layer and the light absorption layer which can be used as the light blocking layer will be described.

(Light Reflection Layer)

Since there is no increase in the temperature of the film according to the use of the light reflection layer which reflects light for light blocking, film durability increases, and thus film performance is easily maintained. In general, the light reflection layer has mirror-like appearance and gives a positive effect to the film appearance. Accordingly, when the layer is used as a sensor component, it is readily used in a portion exposed to the human eye.

Examples of the light reflection layer include a dielectric multi-layer film and a layer having a cholesteric liquid crystalline phase fixed therein.

(Dielectric Multi-Layer Film)

The dielectric multi-layer film is a film obtained by alternately laminating transparent dielectric layers made of an inorganic oxide or an organic polymer and having different refractive indices. At least one of these transparent dielectric layers is configured such that a product (n×d) of a thickness (d) and a refractive index (n) of the transparent dielectric layer is ¼ of a wavelength (λ) of light to be reflected, and thus can reflect light in a region with a reflection bandwidth decided to correspond to a difference in the refractive index between the dielectric layers at the central wavelength λ of the reflection. With a usual combination of materials, it is difficult to cause reflection in an entire desired wavelength region in the dielectric multi-layer film of one period in many cases. Accordingly, several types of layer with different values of n×d, which are different in the central wavelength of reflected light, may be laminated to adjust, for example, widen the reflection bandwidth. The transparent dielectric layer is not particularly limited as long as it has light transmitting properties in a specific wavelength region in which the circular polarization filter selectively transmits either right-handed circularly polarized light or left-handed circularly polarized light.

In general, $TiO_2$, $SiO_2$, $Ta_2O_5$, and the like can be suitably used as the inorganic oxide in the dielectric multi-layer film. The layer made of the inorganic oxide can be formed through a sputtering method or the like on a surface of glass or a heat-resistant polymer film. Examples of the organic polymer material include polycarbonate, acrylic resin, polyester, epoxy resin, polyurethane, polyamide, polyolefin, and silicone (including modified silicone such as silicone polyurea), and the organic polymer material can be produced in accordance with the method disclosed in JP1997-507308A (JP-H9-507308A) or the like.

(Layer Having Cholesteric Liquid Crystalline Phase Fixed Therein: Light Reflection Layer)

The above-described layer having a cholesteric liquid crystalline phase fixed therein can be used as the reflection layer.

The thicker the cholesteric liquid crystal layer, the higher the reflectivity at a reflection wavelength. However, in a usual liquid crystal material, when the thickness is 2 μm to 8 μm, the reflectivity is saturated in, for example, a wavelength region of visible light, and is at most 50% since circularly polarized light on only one side is reflected. In order to reflect light regardless of the sense of circularly polarized light and to adjust the natural light reflectivity to 50% or greater, a layer in which a cholesteric liquid crystal layer having a right-handed helical sense and a cholesteric liquid crystal layer having a left-handed helical sense, which have the same period P, are laminated, or a laminate formed of cholesteric liquid crystal layers having the same period P and the same helical sense and a phase difference film disposed therebetween and having a phase difference of a half wavelength with respect to a central wavelength of the circularly polarized light reflection band of the cholesteric liquid crystal layer can be used as the light reflection layer.

(Light Absorption Layer)

As the light absorption layer, a layer formed by coating a base (which preferably has sufficient light transmitting properties in a wavelength region of infrared rays to be detected by the light receiving element) with a dispersion liquid in which a colorant such as a pigment or a dye is dispersed in a solvent containing a dispersant, a binder, or a monomer, a layer having a polymer base with a surface directly dyed using a dye, or a layer formed from a polymer material containing a dye can be used.

As the pigment, pigments which do not cause absorption or scattering in a specific wavelength region in which the circular polarization filter selectively transmits either right-handed circularly polarized light or left-handed circularly polarized light are preferably used. Therefore, color printing inks of cyan, magenta, yellow, and black requiring transparency, or pigments which are used in red, green, and blue color filters of liquid crystal display devices, organic LED display devices, or the like can be suitably used. By mixing these pigments which have different the wavelengths at which the maximum absorption occurs, it is possible to form a layer for sufficient absorption in an entire desired wavelength region other than the specific wavelength region.

As the dye, a dye which does not cause absorption at a specific wavelength region in which the circular polarization filter selectively transmits either right-handed circularly polarized light or left-handed circularly polarized light, and is durable against light exposure is preferably used. General direct dyes, acid dyes, basic dyes, mordant dyes, disperse dyes, reactive dyes, and the like can be used. As this dye-type absorption layer, commercially available photographic filters IR-80, IR-82, IR-84, and the like (manufactured by Fujifilm Corporation) can be used.

(Light Absorption Layer Provided on Surface in Thickness Direction of Circular Polarization Filter)

As shown in FIGS. 1(a) and 1(d), the circular polarization filter may have the light absorption layer on a surface in the thickness direction. A layer produced in the same manner using the same material as in the light absorption layer as the above-described light blocking layer can be used as the light absorption layer, but the light absorption layer provided on the surface in the thickness direction may absorb light in a specific wavelength region in which the circular polarization filter selectively transmits either right-handed circularly polarized light or left-handed circularly polarized light.

Some or all of the surfaces in the thickness direction may be used. For example, when the circular polarization filter has a rectangular or square shape, all four surfaces thereof may be used, or only one to three surfaces of the rectangular or square circular polarization filter may be used. For example, the light absorption layer may be provided only on a surface in which the quantity of incident light from a side surface (surface in thickness direction) is significant.

(Other Layers)

The circular polarization filter may include other layers such as a support, an alignment layer for alignment of the liquid crystal compound, and an adhesion layer for adhesion between the layers. As in the description of the transparent medium, other layers preferably have transparency, low birefringence, and such a refractive index that the difference between the refractive index and the average refractive index (average in-plane refractive index) of the circularly-polarized light separating layer is small. In addition, other layers preferably do not have properties that offset the optical properties of the light blocking layer and the circularly-polarized light separating layer.

(Support)

The support is not particularly limited. The support which is used to form the circularly-polarized light separating layer, the λ/4 phase difference layer, or the like may be a layer constituting the circular polarization filter as is, or a temporary support to be peeled off after layer formation. When the support is a temporary support, it does not constitute the circular polarization filter, and thus there are no limits related to optical properties such as the above-described transparency and refringence.

Glass and the like may be used as the support (temporary support) in addition to a plastic film. Examples of the plastic film include polyester such as polyethylene terephthalate (PET), polycarbonate, acrylic resin, epoxy resin, polyurethane, polyamide, polyolefin, cellulose derivatives, and silicone.

(Alignment Film)

The alignment film can be provided with means such as a rubbing treatment of an organic compound or a polymer (resins such as polyimide, polyvinyl alcohol, polyester, polyarylate, polyamide-imide, polyether-imide, polyamide, and modified polyamide), oblique deposition of an inorganic compound, formation of a layer having a microgroove, or accumulation of an organic compound (for example, co-tricosanoic acid, dioctadecylmethylammonium chloride, methyl stearate) by a Langmuir-Blodgett method (LB film). Furthermore, an alignment film which generates an alignment function by application of an electric field, application of a magnetic field, or light irradiation is also known. Among these, an alignment film to be formed by a rubbing treatment of a polymer is particularly preferred. The rubbing treatment can be carried out by unidirectionally rubbing several times the surface of a polymer layer with paper or cloth.

Without providing the alignment film, a liquid crystal composition may be applied to a support surface or a rubbed surface of the support.

(Adhesion Layer)

The adhesion layer may be formed from an adhesive.

From the viewpoint of the curing method, examples of the adhesive include hot melt types, thermosetting types, photocurable types, reactive curing types, and pressure sensitive adhesion types which are not required to be cured, and as materials thereof, compounds such as acrylate compounds, urethane compounds, urethane acrylate compounds, epoxy compounds, epoxy acrylate compounds, polyolefin compounds, modified olefin compounds, polypropylene compounds, ethylene vinyl alcohol compounds, vinyl chloride compounds, chloroprene rubber compounds, cyanoacrylate compounds, polyamide compounds, polyimide compounds, polystyrene compounds, and polyvinyl butyral compounds can be used. From the viewpoint of workability and productivity, photocurable types are preferred in terms of the curing method, and from the viewpoint of optical transparency and heat resistance, acrylate compounds, urethane acrylate compounds, epoxy acrylate compounds, and the like are preferably used in terms of the material.

(Uses of Circular Polarization Filter)

The uses of the circular polarization filter are not particularly limited, and the circular polarization filter can be used in light source devices, sensors, optical members, sheets for plant cultivation (agricultural sheets), projectors, and the like. Examples of the light source devices include light source devices which are used for plant cultivation and light source devices which are used in sensor systems using polarized light. The circular polarization filter of the invention is also preferably used as a sensor system by combining a light source and a light receiving element.

When using the circular polarization filter, it is preferable that the light from a light source (natural light such as sunlight may be used) passes via the circularly-polarized light separating layer, and is then emitted from the circular polarization filter via at least the transparent medium. In addition, the light emitted from the circular polarization filter via the circularly-polarized light separating layer after passing via at least the transparent medium is preferably detected by the light receiving element. When the circular polarization filter has the light blocking layer, the light blocking layer may be disposed either on the light incident side or on the light emission side, but is preferably disposed on the light incident side.

(Use of Circular Polarization Filter in Sensor System)

Figure 2:
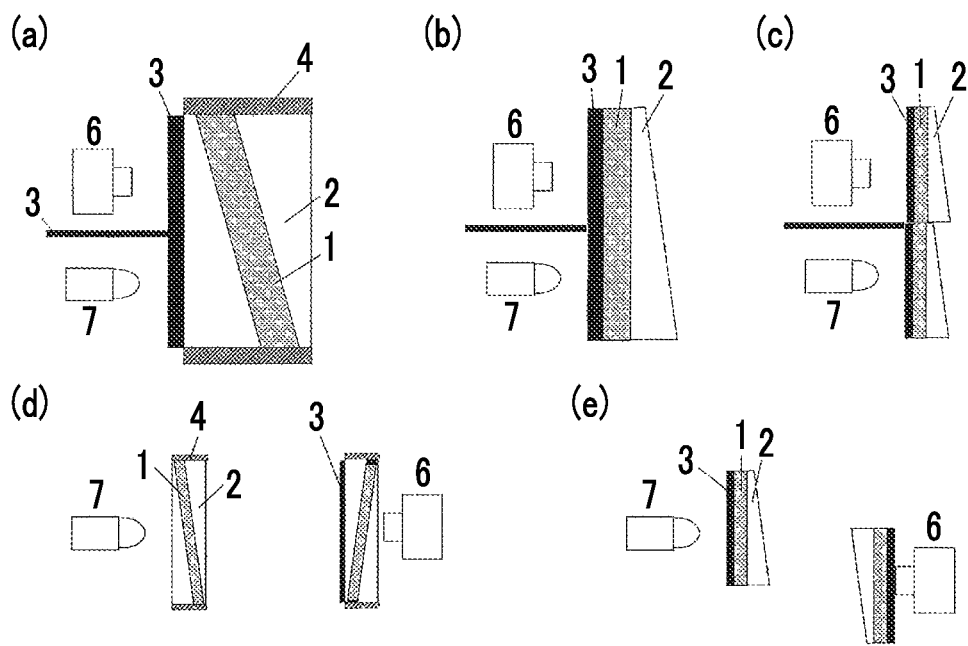
FIG. 2 shows examples in which the circular polarization filter of the invention is used as a sensor system.

An example in which the circular polarization filter of the invention is used as a sensor system will be shown in FIG. 2.

FIGS. 2(a) and 2(b) show examples of a system with a form of detecting reflected light from an object. FIG. 2(a) shows a sensor system using the circular polarization filter of FIG. 1(d), and a light source and a light receiving element are disposed on the light blocking layer side of one circular polarization filter. In the configuration shown in FIG. 2(a), a light blocking layer is provided between the light source and the light receiving element such that the light of the light source is not detected by the light receiving element. As the light blocking layer provided herein, a layer produced in the same manner using the same material as in the light blocking layer which can be used in the above-described circular polarization filter can be used, and the light blocking layer provided between the light source and the light receiving element preferably blocks light in a wavelength region including light in a specific wavelength region in which the circular polarization filter selectively transmits either right-handed circularly polarized light or left-handed circularly polarized light.

FIG. 2(b) shows an example of a sensor system in which a light source and a light receiving element are disposed on one surface of one circular polarization filter of FIG. 1(h). FIG. 2(c) shows an example of a sensor system in which two circular polarization filters of FIG. 1(h) are disposed in series and used as a circular polarization filter on the light source side and as a circular polarization filter on the light receiving element side. Although not shown in the drawings, the light source or the light receiving element may be used in a state of being inclined relative to the circular polarization filter. Even when the light emitted from the light source by the inclined surface in the circular polarization filter enters the filter in a normal direction, the light is emitted at an angle relative to the normal direction due to refraction. Therefore, in the case in which an object to be irradiated is a long distance away, the light source or the light receiving element is preferably used in a state of being inclined relative to the object to be irradiated at an angle set by taking the above case into consideration.

FIGS. 2(d) and 2(e) show examples of a system with a form of detecting transmitted light from an object. FIG. 2(d) shows a sensor system using the circular polarization filters of FIGS. 1(a) and 1(d), and FIG. 2(e) shows a sensor system using two circular polarization filters of FIG. 1(h). In the configuration of FIG. 2(e), the adjustment is preferably performed such that the object is disposed on a path of light emitted from the light source and changed in the angle by refraction in the first circular polarization filter. In addition, the setting position of the light receiving element is preferably adjusted such that the light receiving element is positioned on a path of light transmitted through the object and changed in the angle by refraction in the second circular polarization filter.

(Detection of Object)

The wavelength region of the light used in the sensor system is not particularly limited, but infrared light, particularly, light in a wavelength region of near infrared light is preferred. Using circularly polarized light as light for sensing (detection), optical properties of an object can be reflected as a comparison to the background, and it is possible to detect an object having specific optical properties or to perform the detection with reduced malfunction in the detection of reflected light and transmitted light from an object via a filter having selectivity for circularly polarized light transmitting properties. In addition, when using circularly polarized light, the adjustment of the direction of the filter for polarization detection is facilitated or not required compared to a case of using linearly polarized light as polarized light. In this description, the expression "reflected light and transmitted light" includes scattered light and diffracted light. Examples of the object which can be detected by the sensor system include a crack or a scratch on a transparent (birefringent) film or a specular reflector (metal plate or the like) and foreign substances on a specular reflector. The sensor system may also be used as a motion sensor for security for people such as night pedestrians and a motion sensor of an automatic door, an elevator, or the like.

(Light Receiving Element)

As the light receiving element, a detector in which photodiode-type sensors or light detection elements using a semiconductor such as Si, Gc, HgCdTe, PtSi, InSb, and PbS are linearly arranged, and a CCD and a CMOS capable of capturing an image are included.

In the system using the circular polarization filter of the invention, a light receiving element which can detect light having a wavelength in the controlled wavelength region may be used.

The circular polarization filter may be disposed on, for example, the light receiving surface of a sensor.

When the circular polarization filter and the light receiving element are used as a sensor in an integrated manner, the sensor preferably has a configuration in which the light receiving element is provided in a housing and the circular polarization filter is disposed in a light capturing portion such that light other than light passing via the circular polarization filter does not reach the light receiving element. The sensor preferably includes a light receiving element, a circularly-polarized light separating layer, and a transparent medium in this order. In addition, the sensor preferably includes a light receiving element, a transparent medium, a circularly-polarized light separating layer, and a transparent medium in this order. When a light blocking layer is included, the light blocking layer may be disposed on the light receiving element side or on the outside when viewed from the circularly-polarized light separating layer, but is preferably disposed on the outside. When the circularly-polarized light separating layer is a laminate including a linearly-polarized light separating layer and a $\lambda/4$ phase difference layer, the sensor preferably includes the light receiving element, the linearly-polarized light separating layer, and the $\lambda/4$ phase difference layer in this order.

(Light Source, Light Source Device)

As the light source, a light source capable of emitting light having a wavelength in the controlled wavelength region may be used. Any light source such as a halogen lamp, a tungsten lamp, a LED, a LD, a xenon lamp, or a metal halide lamp can be used as long as it emits light having a photosensitive wavelength of the light receiving element. However, a LED or a LD is preferred in view of small size, light-emitting directivity, monochromatic light, and pulse modulation suitability.

When a light source device is constituted by combining a light source and the above-described circular polarization filter, the light source device preferably has a configuration in which, for example, the light source is provided in a housing and the circular polarization filter is disposed in a light emitting portion such that light other than light passing via the circular polarization filter is not emitted from the light source. The light source device preferably includes a light source, a circularly-polarized light separating layer, and a transparent medium in this order. When a light blocking layer is included, the light blocking layer may be disposed on the light source side or on the outside when viewed from the circularly-polarized light separating layer, but is preferably disposed on the outside. When the circularly-polarized light separating layer is a laminate including a linearly-polarized light separating layer and a $\lambda/4$ phase difference layer, the light source device preferably includes the light source, the linearly-polarized light separating layer, and the $\lambda/4$ phase difference layer in this order.

EXAMPLES

Hereinafter, the invention will be described in more detail using examples. The materials, reagents, amounts and proportions of substances, operations, and the like shown in the following examples may be appropriately modified without departing from the gist of the invention. The scope of the invention is, therefore, not limited to the following examples.

Example 1

A coating liquid A-1 shown in Table 1 was applied to a rubbed surface of PET, manufactured by Fujifilm Corporation, subjected to a rubbing treatment by using a wire bar at room temperature such that the thickness of the dried film after drying was 5 µm. After being dried for 30 seconds at room temperature, the coating layer was heated for 2 minutes under an atmosphere at 85° C., and then UV-irradiated for 6 to 12 seconds using a D-bulb (lamp 90 mW/cm) manufactured by Heraeus K. K. Noblelight Division with an output of 60% at 30° C. to fix a cholesteric liquid crystal layer. Thus, a circularly-polarized light separating layer was obtained.

Figure 3:
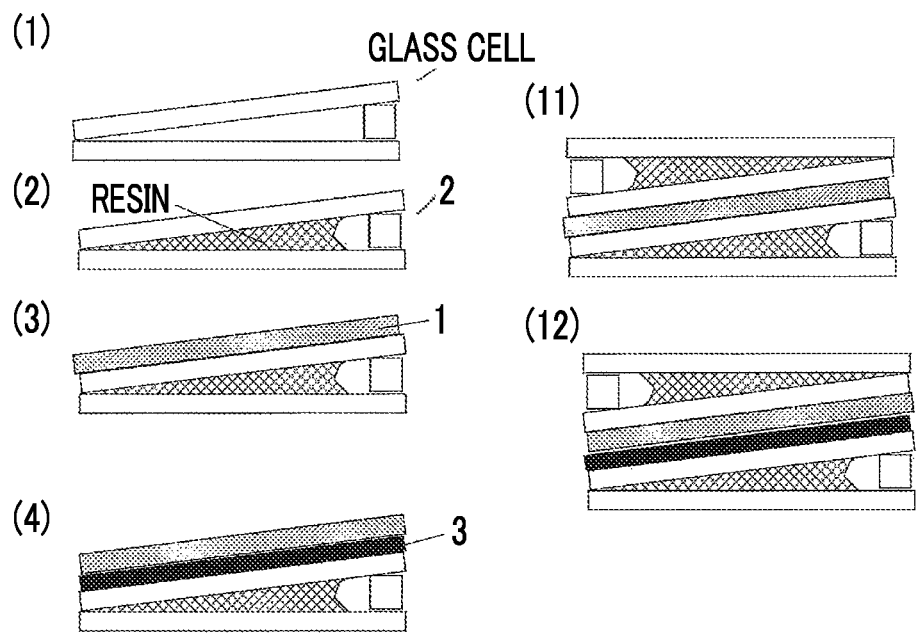
FIG. 3 shows configurations (schematic sectional views) of circular polarization filters used in examples.

Next, a wedge-shaped glass cell having an inclination angle of 3 degrees was formed to have a layer configuration shown in FIG. 3(1), and a mixture of 100 parts by mass of an acrylic monomer NK ester 600 manufactured by Shin-Nakamura Chemical Co., Ltd and 3 parts by mass of a polymerization initiator Irgacure 907 manufactured by Ciba Specialty Chemicals Inc. was injected into the glass cell at room temperature and UV-irradiated at room temperature to resinify and fix the monomer to thereby produce an inclined transparent medium having a layer configuration shown in FIG. 3(2). This cell was observed using a schaukasten having a polarization plate installed on a crossed Nichol prism, and no generation of birefringence was confirmed in the inclined transparent medium.

A UV-curable adhesive Exp. U12034-6 manufactured by DIC Corporation was applied to this inclined transparent medium by using a wire bar at room temperature such that the thickness of the dried film after drying was 5 µm. This coating surface and a surface on the liquid crystal layer side of the circularly-polarized light separating layer produced as described above were stuck together so as to prevent air bubbles from entering therebetween, and then UV-irradiated for 6 to 12 seconds using a D-bulb (lamp 90 mW/cm) manufactured by Heraeus K. K. Noblelight Division with an output of 60% at 30° C. Thereafter, the PET, manufactured by Fujifilm Corporation, as a support of the circularly-polarized light separating layer was peeled off to obtain a circular polarization filter of Example 1 having a layer configuration shown in FIG. 3(3).

Example 2

A circular polarization filter of Example 2 was produced in the same manner as in Example 1, except for using a glass cell having an inclination angle of 8 degrees.

Example 3

A circular polarization filter of Example 3 was produced in the same manner as in Example 1, except for using a glass cell having an inclination angle of 15 degrees.

Example 4

A circular polarization filter of Example 4 was produced in the same manner as in Example 1, except for using a glass cell having an inclination angle of 30 degrees.

Example 5

The same inclined transparent medium as the inclined transparent medium produced in Example 1 using the glass cell having an inclination angle of 3 degrees was adhered to the circularly-polarized light separating layer side of the circular polarization filter of Example 1 in a state of being antiparallel to the inclined transparent medium in the circular polarization filter of Example 1 to produce a circular polarization filter of Example 5 having a layer configuration shown in FIG. 3(11).

Example 6

A circular polarization filter of Example 6 was produced in the same manner as in Example 1, except for using a liquid crystal coating liquid A-2.

Example 7

A coating liquid A-3 shown in Table 1 was applied to a rubbed surface of PET, manufactured by Fujifilm Corporation, subjected to a rubbing treatment by using a wire bar at room temperature such that the thickness of the dried film after drying was 5 µm. After being dried for 30 seconds at room temperature, the coating layer was heated for 2 minutes under an atmosphere at 85° C., and then UV-irradiated for 6 to 12 seconds using a D-bulb (lamp 90 mW/cm) manufactured by Heraeus K. K. Noblelight Division with an output of 60% at 30° C. to obtain a liquid crystal layer. A coating liquid A-4 shown in Table 1 was applied to this liquid crystal layer at room temperature such that the thickness of the dried film after drying was 5 µm, and then drying, heating, and UV irradiation were performed in the same manner as in the above description to form a second liquid crystal layer. A coating liquid A-5 shown in Table 1 was applied to the second liquid crystal layer at room temperature such that the thickness of the dried film after drying was 5 µm, and then drying, heating, and UV irradiation were performed in the same manner as in the above description to form a third liquid crystal layer. Thus, a circularly-polarized light separating layer was obtained.

A UV-curable adhesive Exp. U12034-6 manufactured by DIC Corporation was applied to an inclined transparent medium formed in the same manner as in Example 1 using a glass cell having an inclination angle of 8 degrees by using a wire bar at room temperature such that the thickness of the dried film after drying was 5 µm. An IR80 manufactured by Fujifilm Corporation as a visible light absorption layer was stuck thereto so as to prevent air bubbles from entering therebetween, and then UV-irradiated using a D-bulb manufactured by Heraeus K. K. Noblelight Division at 30° C. The above-described UV-curable adhesive was further applied thereonto in the same manner and stuck to a surface on the liquid crystal layer side of the circularly-polarized light separating layer so as to prevent air bubbles from entering therebetween, and then UV-irradiated in the same manner at 30° C. Thereafter, the PET, manufactured by Fujifilm Corporation, as a support of the circularly-polarized light separating layer was peeled off to obtain a circular polarization filter of Example 7 having a layer configuration shown in FIG. 3(4).

Example 8

The same inclined transparent medium as the inclined transparent medium produced in Example 7 using the glass cell having an inclination angle of 8 degrees was adhered to the circularly-polarized light separating layer side of the circular polarization filter of Example 7 in a state of being antiparallel to the inclined transparent medium in the circular polarization filter of Example 7 to produce a circular polarization filter of Example 8 having a layer configuration shown in FIG. 3(12).

Example 9

A circular polarization filter of Example 9 was produced in the same manner as in Example 8, except that the visible light absorption layer was excluded.

Example 10

A coating liquid A-6 shown in Table 1 was spin-applied to a rubbed surface of PET, manufactured by Fujifilm Corporation, subjected to a rubbing treatment at 2000 rpm. After being dried for 30 seconds at room temperature, the coating layer was heated for 2 minutes under an atmosphere at 85° C., and then UV-irradiated for 6 to 12 seconds using a D-bulb (lamp 90 mW/cm) manufactured by Heraeus K. K. Noblelight Division with an output of 60% at 30° C. to obtain a phase difference film.

The phase difference of this phase difference film was measured at 400 nm to 800 nm using an AXOSCAN of Axometrix. Using these measured values, a phase difference at 880 nm was obtained through an extrapolation method, and a phase difference of 220 nm was obtained.

A UV-curable adhesive Exp. U12034-6 manufactured by DIC Corporation was applied to a phase difference film surface of this film by using a wire bar at room temperature such that the thickness of the dried film after drying was 5 μm. A wire grid polarization plate as a reflective linear polarizer manufactured by Polatechno Co., Ltd. was stuck thereto such that the in-plane angle between an alignment axis of liquid crystal molecules and an absorption axis of the polarization plate was 45 degrees, and thus a circular polarization plate was formed. A circular polarizance was measured using the above-described AXOSCAN by positioning the circular polarization plate on the light incident side, and thus the circular polarization plate was confirmed to be a left-handed circular polarization plate at 800 nm.

A UV-curable adhesive Exp. U12034-6 manufactured by DIC Corporation was applied to an IR80 manufactured by Fujifilm Corporation at room temperature such that the thickness of the dried film after drying was 5 μm. This coating surface and a surface of the linear polarization plate of the circularly-polarized light separating layer produced as described above were stuck together so as to prevent air bubbles from entering therebetween, and then UV-irradiated for 6 to 12 seconds using a D-bulb (lamp 90 mW/cm) manufactured by Heraeus K. K. Noblelight Division with an output of 60% at 30° C. Next, the above-described adhesive was applied to the phase difference film side of the circularly-polarized light separating layer, and an inclined transparent medium formed in the same manner as in Example 1 using a glass cell having an inclination angle of 8 degrees was adhered thereto to produce a circular polarization filter of Example 10.

Comparative Example 1

Only the circularly-polarized light separating layer produced in Example 1 was used.

Comparative Example 2

A circular polarization filter produced in the same manner as in Example 1 was used, except for using a glass cell having an inclination angle of 45 degrees.

Comparative Example 3

A circular polarization filter produced in the same manner as in Example 7 was used, except that the inclined transparent medium formed using a glass cell was not used.

Comparative Example 4

A circular polarization filter produced in the same manner as in Example 10 was used, except that the inclined transparent medium formed using a glass cell was not used.

Comparative Example 5

The circular polarization filter produced in Example 1 was used (light entered from the transparent medium side in the circular polarizance measurement and the like).

TABLE 1

| Material (type) | Name of Material (manufacturer) | Name of Coating Liquid | | | | | |
|---|---|---|---|---|---|---|---|
| | | A-1 | A-2 | A-3 | A-4 | A-5 | A-6 |
| Liquid Crystalline Compound | Compound 1 | 100 parts by mass | 100 parts by mass | 100 parts by mass | 100 parts by mass | 100 parts by mass | 100 parts by mass |
| Polymerization Initiator | Irg-819 (Ciba Specialty Chemicals Inc.) | 4 parts by mass | 4 parts by mass | 4 parts by mass | 4 parts by mass | 4 parts by mass | 4 parts by mass |
| Alignment Control Agent | Compound 2 | 0.03 parts by mass | 0.03 parts by mass | 0.03 parts by mass | 0.03 parts by mass | 0.03 parts by mass | 0.03 parts by mass |
| Chiral Agent | LC-756 (BASF) | 5.4 parts by mass | 8.2 parts by mass | 3.7 parts by mass | 3.5 parts by mass | 3.3 parts by mass | — |
| Solvent | 2-Butanone (Wako Pure Chemical Industries, Ltd.) | Appropriate Adjustment According to Film Thickness | Appropriate Adjustment According to Film Thickness | Appropriate Adjustment According to Film Thickness | Appropriate Adjustment According to Film Thickness | Appropriate Adjustment According to Film Thickness | Appropriate Adjustment According to Film Thickness |

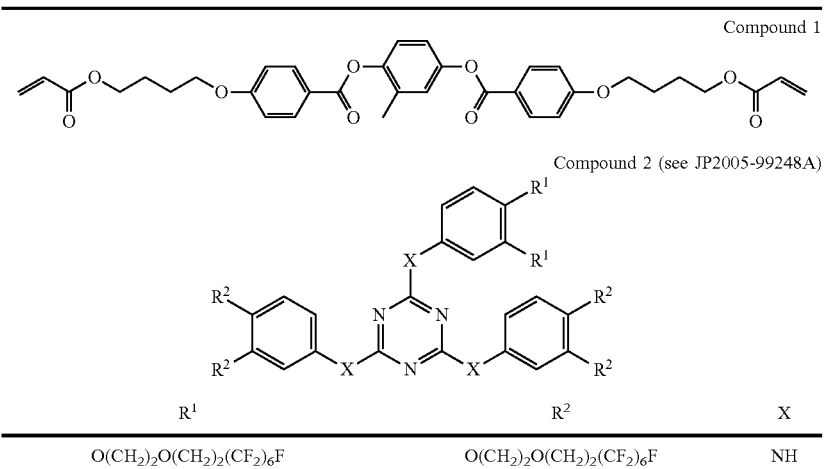

| | R[1] | R[2] | X |
|---|---|---|---|
| | O(CH$_2$)$_2$O(CH$_2$)$_2$(CF$_2$)$_6$F | O(CH$_2$)$_2$O(CH$_2$)$_2$(CF$_2$)$_6$F | NH |

Measurement Method

Figure 4:
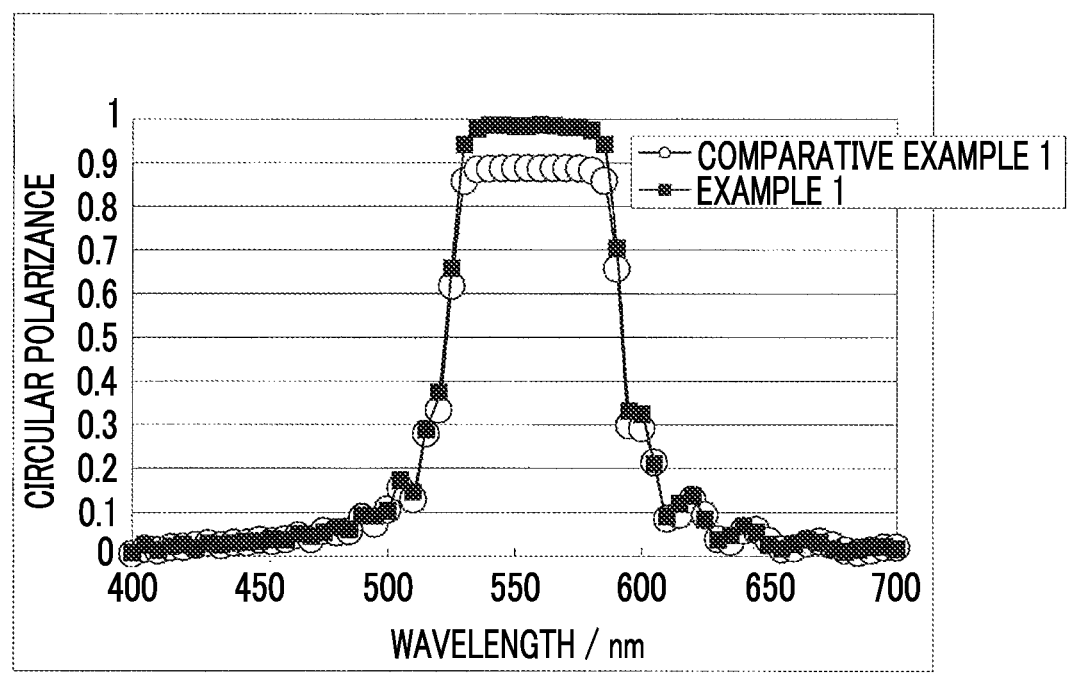
FIG. 4 is a graph showing results of the measurement of circular polarizances at wavelengths of 400 nm to 700 nm obtained in the circular polarization filters of Example 1 and Comparative Example 1.

With respect to a sample of which the selective reflection wavelength was within a range of 400 nm to 800 nm, a circular polarizance of transmitted light was measured with a wavelength step of 5 nm using an AXOSCAN of Axometrix. In Examples 1 to 5 and Comparative Examples 1 and 2, the measurement was performed such that the sample was disposed to allow measurement light to enter from the circularly-polarized light separating layer side, and in Comparative Example 5, the measurement was performed such that the sample was disposed to allow measurement light to enter from the transparent medium side. In the measurement, the inclinations of a light source of the sample filter and a detector were adjusted such that the maximum light transmittance was reached. Measurement results of Example 1 and Comparative Example 1 are shown in FIG. 4. Values obtained by reading the circular polarizance at the selective reflection wavelength in the drawing are shown in Table 2. The maximum circular polarizances measured in Examples 1 to 5 and Comparative Examples 1, 2, and 5 are shown in Table 3.

TABLE 2

| | Circular Polarizance | |
|---|---|---|
| Wavelength (nm) | Comparative Example 1 | Example 1 |
| 400 | 0.004887 | 0.008711 |
| 405 | 0.016723 | 0.026299 |
| 410 | 0.012886 | 0.014013 |
| 415 | 0.020493 | 0.022674 |
| 420 | 0.020876 | 0.02572 |
| 425 | 0.025681 | 0.018973 |
| 430 | 0.029874 | 0.028927 |
| 435 | 0.024773 | 0.025897 |
| 440 | 0.03028 | 0.029591 |
| 445 | 0.030646 | 0.032657 |
| 450 | 0.036689 | 0.03498 |
| 455 | 0.034366 | 0.038902 |
| 460 | 0.038092 | 0.037643 |
| 465 | 0.046862 | 0.051471 |
| 470 | 0.038364 | 0.04571 |
| 475 | 0.057132 | 0.05457 |
| 480 | 0.053616 | 0.065479 |
| 485 | 0.056784 | 0.060647 |
| 490 | 0.088284 | 0.093161 |
| 495 | 0.07313 | 0.092033 |
| 500 | 0.106145 | 0.103316 |
| 505 | 0.154831 | 0.173135 |
| 510 | 0.129459 | 0.145034 |

TABLE 2-continued

| | Circular Polarizance | |
|---|---|---|
| Wavelength (nm) | Comparative Example 1 | Example 1 |
| 515 | 0.278971 | 0.2882 |
| 520 | 0.333502 | 0.373547 |
| 525 | 0.617597 | 0.657025 |
| 530 | 0.856804 | 0.942032 |
| 535 | 0.884564 | 0.977317 |
| 540 | 0.886392 | 0.986279 |
| 545 | 0.887034 | 0.986478 |
| 550 | 0.887503 | 0.983924 |
| 555 | 0.887542 | 0.984117 |
| 560 | 0.886981 | 0.987276 |
| 565 | 0.887152 | 0.985263 |
| 570 | 0.88772 | 0.982216 |
| 575 | 0.886605 | 0.982021 |
| 580 | 0.881929 | 0.973802 |
| 585 | 0.858125 | 0.94219 |
| 590 | 0.657514 | 0.703564 |
| 595 | 0.297435 | 0.331986 |
| 600 | 0.291196 | 0.323733 |
| 605 | 0.213615 | 0.210086 |
| 610 | 0.085437 | 0.091058 |
| 615 | 0.094599 | 0.119779 |
| 620 | 0.128644 | 0.138185 |
| 625 | 0.093562 | 0.0838 |
| 630 | 0.03891 | 0.036979 |
| 635 | 0.032572 | 0.048042 |
| 640 | 0.057904 | 0.069413 |
| 645 | 0.05984 | 0.054895 |
| 650 | 0.035426 | 0.02695 |
| 655 | 0.015775 | 0.017887 |
| 660 | 0.01828 | 0.028228 |
| 665 | 0.02985 | 0.037487 |
| 670 | 0.033847 | 0.032137 |
| 675 | 0.025604 | 0.01828 |
| 680 | 0.012895 | 0.010642 |
| 685 | 0.007856 | 0.014226 |
| 690 | 0.013318 | 0.021238 |
| 695 | 0.020145 | 0.022363 |
| 700 | 0.020159 | 0.016955 |
| 705 | 0.014624 | 0.009673 |
| 710 | 0.00759 | 0.007176 |
| 715 | 0.004836 | 0.009478 |
| 720 | 0.008908 | 0.014056 |
| 725 | 0.012596 | 0.013642 |
| 730 | 0.013343 | 0.011198 |
| 735 | 0.010342 | 0.006597 |
| 740 | 0.006817 | 0.004856 |
| 745 | 0.003719 | 0.005045 |
| 750 | 0.003422 | 0.0069 |
| 755 | 0.005038 | 0.008669 |
| 760 | 0.008143 | 0.00833 |

TABLE 2-continued

| | Circular Polarizance | |
|---|---|---|
| Wavelength (nm) | Comparative Example 1 | Example 1 |
| 765 | 0.008589 | 0.007256 |
| 770 | 0.007547 | 0.00431 |
| 775 | 0.004852 | 0.00365 |
| 780 | 0.002945 | 0.003542 |
| 785 | 0.002054 | 0.004387 |
| 790 | 0.003087 | 0.005709 |
| 795 | 0.003908 | 0.006096 |
| 800 | 0.005643 | 0.005572 |

To measure a circular polarizance with respect to a sample (Examples 6 to 10 and Comparative Examples 3 and 4) of which the selective reflection wavelength was not within the wavelength region of 400 nm to 800 nm, the reflectivity was measured with the use of a visible/ultraviolet/near infrared reflective spectrometer by using an optical mirror as a reflector and by disposing the same sample on both the incident light side and the detector side such that the transparent medium side faced the optical mirror side. In the measurement, the inclination of the optical mirror relative to the sample filter was adjusted such that the intensity of the detected light was maximum. The measured maximum circular polarizances are shown in Table 3.

Figure 5:
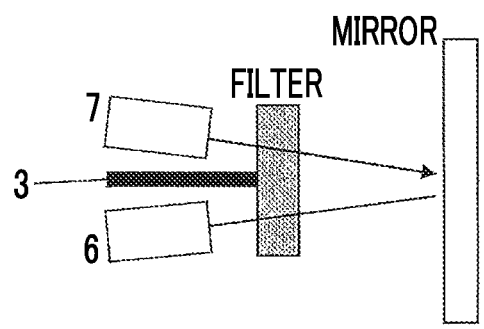
FIG. 5 is a diagram schematically showing the arrangement of a filter, a light source, a light receiving element, and a mirror used in the examples.

Evaluation of Performance as Circular Polarization Filter for Photoelectric Sensor An evaluation of performance as a circular polarization filter for a photoelectric sensor was performed with respect to the filters of Examples 7 to 10 and Comparative Examples 3 and 4 produced as described above. The filter, mirror, light source (KED880S4 manufactured by Kyosemi Corporation), and light receiving element (KS 1364 manufactured by Shinko Denshi Co. Ltd.) were disposed as shown in FIG. 5. In Examples 7 and 10, the transparent medium was disposed on the mirror side, and in Example 8 and Comparative Examples 3 and 4, the circularly-polarized light separating layer was disposed on the mirror side with respect to the light blocking layer. Unpolarized light having a central wavelength of 880 nm was applied from the light source to the mirror via the filter, and the light reflected from the mirror and transmitted through the filter was detected by the light receiving element to perform the evaluation. In the measurement, the inclination of the mirror was adjusted such that the intensity detected when the filter was installed was maximum. The value measured when no filter was installed was set to 100, and the evaluation was performed by correcting the value measured when the filter was installed. The lower the value, the more effective. The evaluation criteria are as follows. The measurement was performed in a state in which the light was completely blocked in the dark room and an incandescent lamp was turned on in the light room. The results are shown in Table 3.

AA: 0 to 3
A: 3 to 10
B: 10 to 25
C: 25 to 50
D: 50 to 100
E: 100 or greater

TABLE 3

| | Circularly-polarized light separating layer | | | Inclination Angle ° | | Configuration of Circular Polarization Filter | Visible Light Blocking Layer | Circular Polarizance Measurement Result | Reflection Measurement Result | |
|---|---|---|---|---|---|---|---|---|---|---|
| | Selective Reflection Layer | Short Wave nm | Long Wave nm | Wavelength band nm | Light Emission Side | Light Source Side | | | | Dark Room | Light Room |
| Example 1 | Cholesteric | 525 | 590 | 65 | 3 | — | FIG. 3(3) | None | 0.99 | | |
| Example 2 | Cholesteric | 525 | 590 | 65 | 8 | — | FIG. 3(3) | None | 1 | | |
| Example 3 | Cholesteric | 525 | 590 | 65 | 15 | — | FIG. 3(3) | None | 0.99 | | |
| Example 4 | Cholesteric | 525 | 590 | 65 | 30 | — | FIG. 3(3) | None | 0.96 | | |
| Example 5 | Cholesteric | 525 | 590 | 65 | 8 | 8 | FIG. 3(11) | None | 0.99 | | |
| Example 6 | Cholesteric | 350 | 395 | 45 | 8 | — | FIG. 3(3) | None | 0.98 | | |
| Example 7 | Cholesteric | 800 | 910 | 110 | 8 | — | FIG. 3(4) | Absorption Layer | 0.99 | AA | AA |
| Example 8 | Cholesteric | 800 | 910 | 110 | 8 | 8 | FIG. 3(12) | Absorption Layer | 0.99 | AA | AA |
| Example 9 | Cholesteric | 800 | 910 | 110 | 8 | 8 | FIG. 3(11) | None | 0.99 | AA | A |
| Example 10 | Reflective Linear Pol + λ/4 Plate | 400 | 1200 | 600 | 8 | — | FIG. 3(4) | Absorption Layer | 0.99 | AA | AA |
| Comparative Example 1 | Cholesteric | 525 | 590 | 65 | None | None | — | None | 0.88 | | |
| Comparative Example 2 | Cholesteric | 525 | 590 | 65 | 45 | 45 | FIG. 3(3) | None | 0.91 | | |
| Comparative Example 3 | Cholesteric | 800 | 910 | 110 | — | — | — | Absorption Layer | 0.87 | A | A |
| Comparative Example 4 | Reflective Linear Pol + λ/4 Plate | 800 | 910 | 110 | — | — | — | Absorption Layer | 0.86 | A | A |
| Comparative Example 5 | Cholesteric | 525 | 590 | 65 | 3 | — | FIG. 3(3) | None | 0.88 | | |

EXPLANATION OF REFERENCES

1: circularly-polarized light separating layer

2: transparent medium

3: light blocking layer

4: light absorption layer

6: light receiving element

7: light source

What is claimed is:

1. A sensor system comprising:
    a sensor comprising:
        a circular polarization filter and a light receiving element, the circular polarization filter comprising a circularly-polarized light separating layer,
        wherein the circularly-polarized light separating layer selectively transmits either right-handed circularly polarized light or left-handed circularly polarized light in a specific wavelength region,
        a transparent medium which is transparent with respect to light in the specific wavelength region is provided at least on one surface side of the circularly-polarized light separating layer,
        the transparent medium has an inclined surface which forms an angle of 1° to 30° relative to the surface on the transparent medium side of the circularly-polarized light separating layer, and
        the light receiving element being capable of detecting light having a wavelength in the specific wavelength region, and
    a light source which emits light having a wavelength in the specific wavelength region,
    wherein the light source, the circularly-polarized light separating layer, and the transparent medium are disposed in this order.

2. The sensor system according to claim 1,
    wherein the circularly-polarized light separating layer is a layer having a cholesteric liquid crystalline phase fixed therein.

3. The sensor system according to claim 1,
    wherein the circularly-polarized light separating layer is a laminate including a reflective linear polarizer and a λ/4 phase difference layer.

4. The sensor system according to claim 1,
    wherein the transparent medium is directly brought into contact with or directly adhered to the circularly-polarized light separating layer.

5. The sensor system according to claim 1,
    wherein the transparent medium is a uniform medium.

6. The sensor system according to claim 5,
    wherein the difference between a refractive index of the transparent medium and an average in-plane refractive index of the circularly-polarized light separating layer is not greater than 0.05.

7. The sensor system according to claim 1,
    wherein the inclined surface is an outermost surface.

8. The sensor system according to claim 1, which has the transparent medium on both surfaces of the circularly-polarized light separating layer and has a uniform film thickness.

9. The sensor system according to claim 1,
    wherein the specific wavelength region is a wavelength region, having a width of at least 50 nm or greater, within a range of 800 nm to 1500 nm.

10. The sensor system according to claim 9, further comprising:
    a light blocking layer which blocks light in a wavelength region, having a width of 50 nm or greater, within a range of 380 nm to 780 nm.

11. The sensor system according to claim 1, further comprising:
    a light blocking layer which blocks light in at least a part of a wavelength region excluding the specific wavelength region.

12. The sensor system according to claim 1,
    wherein the light receiving element, the circularly-polarized light separating layer, and the transparent medium are disposed in this order.

13. A sensor comprising:
    a circular polarization filter and a light receiving element, the circular polarization filter comprising a circularly-polarized light separating layer,
    wherein the circularly-polarized light separating layer selectively transmits either right-handed circularly polarized light or left-handed circularly polarized light in a specific wavelength region,
    a transparent medium which is transparent with respect to light in the specific wavelength region is provided at least on one surface side of the circularly-polarized light separating layer,
    the transparent medium has an inclined surface which forms an angle of 1° to 30° relative to the surface on the transparent medium side of the circularly-polarized light separating layer, and
    the light receiving element being capable of detecting light having a wavelength in the specific wavelength region,
    wherein the transparent medium is directly brought into contact with or directly adhered to the circularly-polarized light separating layer.

14. A sensor comprising:
    a circular polarization filter and a light receiving element, the circular polarization filter comprising a circularly-polarized light separating layer,
    wherein the circularly-polarized light separating layer selectively transmits either right-handed circularly polarized light or left-handed circularly polarized light in a specific wavelength region,
    a transparent medium which is transparent with respect to light in the specific wavelength region is provided at least on one surface side of the circularly-polarized light separating layer,
    the transparent medium has an inclined surface which forms an angle of 1° to 30° relative to the surface on the transparent medium side of the circularly-polarized light separating layer, and
    the light receiving element being capable of detecting light having a wavelength in the specific wavelength region,
    wherein the transparent medium is a uniform medium, and
    wherein the difference between a refractive index of the transparent medium and an average in-plane refractive index of the circularly-polarized light separating layer is not greater than 0.05.

15. A sensor comprising:
    a circular polarization filter and a light receiving element, the circular polarization filter comprising a circularly-polarized light separating layer,
    wherein the circularly-polarized light separating layer selectively transmits either right-handed circularly polarized light or left-handed circularly polarized light in a specific wavelength region,
    a transparent medium which is transparent with respect to light in the specific wavelength region is provided at least on one surface side of the circularly-polarized light separating layer,
    the transparent medium has an inclined surface which forms an angle of 1° to 30° relative to the surface on the transparent medium side of the circularly-polarized light separating layer, and the light receiving element being capable of detecting light having a wavelength in the specific wavelength region, the transparent medium being on both surfaces of the circularly-polarized light separating layer and has a uniform film thickness.

* * * * *